US007026328B2

(12) United States Patent
Konradi et al.

(10) Patent No.: US 7,026,328 B2
(45) Date of Patent: Apr. 11, 2006

(54) HETEROCYCLIC COMPOUNDS WHICH INHIBIT LEUKOCYTE ADHESION MEDIATED BY $\alpha_4$ INTEGRINS

(75) Inventors: Andrei W. Konradi, Burlingame, CA (US); Christopher M. Semko, Fremont, CA (US); Ying-zi Xu, Palo Alto, CA (US); Frank Stappenbeck, San Francisco, CA (US); Brian P. Stupi, Moss Beach, CA (US); Jenifer L. Smith, Daly City, CA (US); Michael A. Pleiss, Sunnyvale, CA (US); Eugene D. Thorsett, Kirkland, WA (US)

(73) Assignees: Elan Pharmaceuticals, Inc., South San Francisco, CA (US); Wyeth, Madison, NJ (US)

( * ) Notice: Subject to any disclaimer, the term of this patent is extended or adjusted under 35 U.S.C. 154(b) by 26 days.

(21) Appl. No.: 10/447,308

(22) Filed: May 27, 2003

(65) Prior Publication Data

US 2004/0138243 A1 Jul. 15, 2004

Related U.S. Application Data

(60) Provisional application No. 60/383,020, filed on May 24, 2002.

(51) Int. Cl.
*C07D 239/50* (2006.01)
*A61K 31/505* (2006.01)

(52) U.S. Cl. .................. 514/275; 544/323; 544/325
(58) Field of Classification Search ............... 544/323, 544/325; 514/275
See application file for complete search history.

(56) References Cited

U.S. PATENT DOCUMENTS

| 4,018,913 A | 4/1977 | Okamoto et al. |
| 4,018,915 A | 4/1977 | Okamoto et al. |
| 4,036,955 A | 7/1977 | Okamoto et al. |
| 4,041,156 A | 8/1977 | Okamoto et al. |
| 4,046,876 A | 9/1977 | Okamoto et al. |
| 4,055,636 A | 10/1977 | Okamoto et al. |
| 4,055,651 A | 10/1977 | Okamoto et al. |
| 4,070,457 A | 1/1978 | Okamoto et al. |
| 4,073,914 A | 2/1978 | Kikumoto et al. |
| 4,085,057 A | 4/1978 | Masuda et al. |
| 4,096,255 A | 6/1978 | Kikumoto et al. |
| 4,104,392 A | 8/1978 | Okamoto et al. |
| 4,235,871 A | 11/1980 | Papahadjopoulos et al. |
| 4,438,122 A | 3/1984 | Holmwood et al. |
| 4,501,728 A | 2/1985 | Geho et al. |
| 4,505,910 A | 3/1985 | Bagli |
| 4,518,600 A | 5/1985 | Holmwood et al. |
| 4,544,402 A | 10/1985 | Schnurbusch et al. |
| 4,559,345 A | 12/1985 | Gomarasca et al. |
| 4,672,065 A | 6/1987 | Spatz |
| 4,837,028 A | 6/1989 | Allen et al. |
| 4,908,368 A | 3/1990 | Murase et al. |
| 4,959,364 A | 9/1990 | Mueller et al. |
| 4,992,439 A | 2/1991 | Meanwell |
| 5,023,252 A | 6/1991 | Hseih et al. |
| 5,030,644 A | 7/1991 | Baldwin et al. |
| 5,120,734 A | 6/1992 | Klausener et al. |
| 5,238,934 A | 8/1993 | Knüppel et al. |
| 5,278,184 A | 1/1994 | Artico et al. |
| 5,510,332 A | 4/1996 | Kogan et al. |
| 5,580,868 A | 12/1996 | Lunkenheimer et al. |
| 5,770,573 A | 6/1998 | Arrhenius et al. |
| 5,814,643 A | 9/1998 | Duggan et al. |
| 5,861,429 A | 1/1999 | Sato et al. |
| 5,925,644 A | 7/1999 | Jakobi et al. |
| 5,942,504 A | 8/1999 | Grobelny |
| 5,955,491 A | 9/1999 | Sohda et al. |
| 5,962,479 A | 10/1999 | Chen |
| 5,972,946 A | 10/1999 | Murata et al. |
| 6,005,117 A | 12/1999 | Wehner et al. |
| 6,492,372 B1 | 12/2002 | Konradi et al. ........ 514/252.18 |

FOREIGN PATENT DOCUMENTS

| DE | 2655636 | 6/1977 |
| DE | 19536891 | 4/1997 |
| DE | 19713000 | 1/1998 |
| EP | 0116494 | 1/1988 |
| EP | 0288176 | 10/1988 |
| EP | 0330506 | 8/1989 |
| EP | 0147211 | 12/1990 |
| EP | 0535521 | 7/1993 |
| EP | 0526348 | 2/1998 |
| HU | 169926 | 2/1977 |
| JP | 59212480 | 1/1984 |

(Continued)

OTHER PUBLICATIONS

Casanova et al., PubMed Abstract (Rev Neurol. 28(9):909-15), May 1999.*

(Continued)

*Primary Examiner*—Deepak Rao
(74) *Attorney, Agent, or Firm*—Foley & Lardner LLP

(57) ABSTRACT

Disclosed are compounds which bind $\alpha_4$ integrins, preferably VLA-4. Certain of these compounds also inhibit leukocyte adhesion and, in particular, leukocyte adhesion mediated by $\alpha_4$ integrins, preferably VLA-4. Such compounds are useful in the treatment of inflammatory diseases in a mammalian patient, e.g., human, such as asthma, Alzheimer's disease, atherosclerosis, AIDS dementia, diabetes, inflammatory bowel disease, rheumatoid arthritis, tissue transplantation, tumor metastasis and myocardial ischemia. The compounds can also be administered for the treatment of inflammatory brain diseases such as multiple sclerosis.

18 Claims, No Drawings

FOREIGN PATENT DOCUMENTS

| | | |
|---|---|---|
| WO | WO 91/05038 | 4/1991 |
| WO | WO 92/16549 | 10/1992 |
| WO | WO 93/12809 | 7/1993 |
| WO | WO 96/01644 | 1/1996 |
| WO | WO 96/22966 | 8/1996 |
| WO | WO 96/32383 | 10/1996 |
| WO | WO 97/23451 | 7/1997 |
| WO | WO 97/48726 | 12/1997 |
| WO | WO 98/00395 | 1/1998 |
| WO | WO 98/22430 | 5/1998 |
| WO | WO 98/33783 | 8/1998 |
| WO | WO 98/53814 | 12/1998 |
| WO | WO 98/53817 | 12/1998 |
| WO | WO 99/06390 | 2/1999 |
| WO | WO 99/06391 | 2/1999 |
| WO | WO 99/06431 | 2/1999 |
| WO | WO 99/06432 | 2/1999 |
| WO | WO 99/06433 | 2/1999 |
| WO | WO 99/10312 | 3/1999 |
| WO | WO 99/10313 | 3/1999 |
| WO | WO 99/37605 | 7/1999 |
| WO | WO 99/37618 | 7/1999 |
| WO | WO 99/52898 | 10/1999 |
| WO | WO 00/18759 | 4/2000 |
| WO | WO 00/31067 | 6/2000 |

OTHER PUBLICATIONS

Tarkowski et al., PubMed Abstract (Int Arch Allergy Immunol. 121(1):25-33), Jan. 2000.*
Damasio, Alzheimer's Disease and Related Dementias, Cecil Textbook of Medicine, 20th Edition, vol. 2, pp. 1992-6, 1996.*
Piraino, P.S. et al., "Prolonged reversal of chronic experimental allergic encephalomyelitis using a small molecule inhibitor of α4 integrin," *Journal of Neuroimmunology*, 131:147-159 (2002).
Miller, S. D., et al., "Colloquium C15: Comparison of the ability of anit-VLA-4 antibody and a small molecule VLA-4 antagonist to regulate ongoing relapsing EAE," *Journal of Neurochemistry*, C15-02, 85: (Suppl. 1).
Miller, D.H., "Colloquium C15: Natalizumab (anti-VLA4 antibody) in multiple sclerosis," *Journal of Neurochemistry*, C15-04, 85: (Suppl. 1) (2003).
Sandbom, et al., "Biologic Therapy of Inflammatory Bowel Disease," *Gastroenterology*, 122:1592-1608 (2002).
Tilley et al., "VLA-4 antagonists," *Drugs of the Future*, 26(10):289-998 (2001).
Elices et al., "VCAM-1 on Activated Endothelium Interacts with the Leukocyte Integrin VLA-4 at a Site Distince from the VLA-4/Fibronectin Binding Site" *Cell* 60:577-584 (1990).
Springer, Timothy A., "Adhesion receptors of the immune system" *Nature* 346:425-434 (1990).
Osborne, Laurelee, "Leukocyte Adhesion to Endothelium in Inflammation" *Cell* 62:3-6 (1990).
Vedder et al., "Role of neutrophils in generalized reperfusion injury associated with resuscitation from shock" *Surgery* 106:509-516 (1989).
Pretolani et al., "Antibody to Very Late Activation Antigen 4 Prevents Antigen-induced bronchial Hyperreactivity and Cellular Infiltration in the Guinea Pig Airways" *J. Exp. Med.* 180:795-805 (1994).
Abraham et al., "$α_4$-Integrins Mediate Antigen-induced Late Bronchial Responses and Prolonged Airway Hyperresponsiveness in Sheep" *J. Clin. Invest.* 93:776787 (1994).

Mulligan et al., "Role of $β_1$, $β_2$ Integrins and ICAM-1 in Lung Injury after Deposition of IgG and Iga Immune Complexes" *J. Immunology* 150:2407-2417 (1993).
Cybulsky et al. "Endothelial Expression of a Mononuclear Leukocyte Adhesion Molecule During Atherogenesis" *Science* 251:788-791 (1991).
Li et al. "An Atherogenic Diet Rapidly Induces VCAM-1, a Cytokine-Regulatable Mononuclear Leukocyte Adhesion Molecule, in Rabbit Aortic Endothelium" *Arterioscler. Thromb* 13:197-204 (1993).
Sasseville et al. "Monocyte Adhesion to Endothelium in Simian Immunodeficiency Virus-Induced AIDS Encephalitis is Mediated by Vascular Cell Adhesion Molecule-1/α4β1 Integrin Interactions" *Am. J. Path*, 144: 27-40 (1994).
Yang et al "Inhibition of insulitis and prevention of diabetes in nonobese diabetic mice by blocking L-selectin and very late antigen 4 adhesion receptors" *Proc. Nat. Acad. Science (USA)* 90:10494-10498 (1993).
Burkly et al. "Protection Against Adoptive Transfer of Autoimmune Diabetes Mediated Through Very Late Antigen-4 Integrin" *Diabetes* 43:529-534 (1994).
Baron et al. "The Pathogenesis of Adoptive Murine Autoimmune Diabetes Requires an Interaction between α4-Integrins and Vascular Cell Adhesion Molecule" *J. Clin. Invest.*, 93:1700-1708 (1994).
Hamann et al. "Role of $α_4$-Integrins in Lymphocyte Homing to Muscosal Tissues In Vivo" *Immunology*, 152:3282-3293 (1994).
Yednock et al. "Prevention of experimental autoimmune encephalomyelitis by antibodies against α4β integrin" *Nature* 356:63 (1992).
Baron et al. "Surface Expression of α4 Integrin by CD4 T Cells Is Required for Their Entry into Brain Parenchyma" *J. Exp. Med.* 177:57-68 (1993).
vanDinther-Janssen et al. "The VLA-4/VCAM-1 Pathway is Involved in Lymphocyte Adhesion to Endothelium in rheumatoid Synovium" *J. Immunology*, 147:4207-4210 (1991).
vanDinther-Janssen et al. "Role of the CS1 adhesion motif of fibronectin in T cell adhesion to synovial membrane and peripheral lymph node endothelium" *Annals. Rheumatic Dis.*, 52:672-676 (1993).
Elices et al. "Expression and Functional Significance of Alternatively Spliced CS1 Fibronectin in Rheumatoid Arthritis Microvasculature" *J. Clin. Invest.* 93:405-416 (1994).
Postigo et al. "Increased Binding of Synovial T Lymphocytes from Rheumatoid Arthritis to Endothelial-Leukocyte Adhesion Molecule-1 (LAM-1) and Vascular Cell Adhesion Molecule-1 (VCAM-1)" *J. Clin. Invest.*, 89:1445-1452 (1992).
Paul et al. "Monoclonal Antibodies Against LFA-1 and VLA-4 Inhibit Graft Vasculitis in Rat Cardiac Allografts" *Transpl. Proceed.*, 25:813-814 (1993).
Okarhara et al. "Involvement of Very Late Activation Antigen 4 (VLA-4) and Vascular Cell Adhesion Molecule 1 (VCAM-1) in Tumor Necrosis Factor α Enhancement of Experimental Metastasis" *Can. Res.* 54:3233-3236 (1994).
Paavonen et al. "In Vivo Evidence of the Role of α4β1-VCAM-1 Interaction in Sarcoma, but not in Carcinoma Extravasation" *Int. J. Can.* 58:298-302 (1994).
Schadendorf et al. "Tumour Progression an Metastatic Behaviour In Vivo Correlates with Integrin Expression on Melanocytic Tumours" *J. Path*. 170:429-434 (1993).

Bao et al. "Correlation of VLA-4 integrin expression with metastatic potential in various human tumour cell lines" *Diff.* 52:239-246 (1993).

Lauri et al. "Decreased adhesion to endothelial cells and matrix proteins of H-2K gene transfected tumour cells" *British J. Cancer*, 68:862-867 (1993).

Kawaguchi et al. "VLA-4 Molecules on Tumor Cells initiate and Adhesive Interaction with VCAM-1 Molecules on Endothelial Cell Surface" *Japanese J. Cancer Res.* 83:1304-1316 (1992).

Abraham, et al. "Blockade of Late-phase Airway Responses and Airway Hyperresponsiveness in Allergic Sheen with a Small-molecule Peptide Inhibitor of VLA-4" *Am. J. Resper Crit. Care Med.* 156:696-703 (1997).

Advani, et al. "Potential Antineoplastic Agents: N-(2-Benzoxazolyl) amino Acid Esters" *J. of Pharm. Sci.* 57(10) 1693-1696 (1968).

Anderson, et al. "Acute kidney graft rejection" *APMIS* 102, 23-37 (1994).

Anderson, et al. "Process Development of 5-Fluoro-3-[3-[4-(5-methoxy-4-pyrimidinyl)-1-piperazinyl]propyl]-1*H*-indole Dihydrochloride" *Om. Proc. Res. Devel.* 1:300-310 (1997).

Chen, et al. "Mediation of sperm-egg fusion: evidence that mouse egg $\alpha_6\beta_1$ integrin is the receptor for sperm fertilinβ" *Chem. Biol.* 6:1-10 (1999).

Coito, et al. "Blockade of Very Late Antigen-4 Integrin Binding to Fibronectin in Allograft Recipients" *Transplantation* 65:699-706 (1998).

Marr-Leisy, et al. "The comparative spreading behavior of enantiomeric and racemic tyrosine amphiphiles" Colloid & Polumer Sci. 263:791-798 (1985).

Elewaut, et al. "Distinctive Activated Cellular Subsets in Colon from Patients with Crohn's Disease and Ulcerative Colitis" *Scand. J. Gastroenterol* 33:743-748 (1998).

Ewenson, et al. "Analogues of substance P containing an α-hydroxy, β-amino acid: synthesis and biological activity" *Eur. J. Med. Chem.* 26: 435-442 (1991).

Feedman, et al. "Adhesion of Follicular Lymphoma Cells to Lymphoid germinal Centers—A Potential Mechanism of Tumor Cell Homing Following Autologous Transplantation" *Leuk And Lymphoma* 13:47-.

Georczynski, et al. "Manipulation of skin graft rejection in alloimmune mice by anti-VCAM-1:VLA-4 but not anti-ICAM-1:LEA-1 monoclonal antibodies" *Trans. Immunol.* 3:55-61 (1995).

Georczynski, et al. "Altered patters of migration of cytokine-producing T lymphocytes in skin-grafted naïve or immune mice following in vivo administration of anti-VCAM-1 or ICAM-1" *Immunology* 87:573-580 (1996).

Giardina, et al. "Selective κ-Opioid Agonists: Synthesis and Structure-Activity FRelationships of Piperidines Incorporating an Oxo-Containing Acyl Group" *J. Med. Chem.* 37: 3482-3491 (1994).

Gordeev, M.F., "Combinatorial Approaches to Pharmacophoric Heterocycles: A Solid-Phase Synthesis of 3,1-Benzoxazine-4-Ones" *Biotech and Bioengineering* 61 (1) 13-16 (1988).

Grayson, et al. $\alpha d\beta 2$ Integrin Is Expressed on Human Eosinophils and Functions as an Alternative Ligand for Vascular Cell Adhesion Molecule 1 (VCAM-1) *J. Exp. Med.* 188(11) 2187-2191 (1998).

Hartman, et al. "Synthesis and Activity of Novel Nitropyrazines for use as Hypoxic Cell radiosensitisers" *J. Med. Chem.* 27:1634-1639 (1984).

Henke, et al. "N-(2-Benzoylphenyl)-L-tyrosine PPARγ Agonists. 1. Discovery of a Novel Series of Ptent Antihyperglycemic and Antihyperlipidemic Agents" *J. Med. Chem.* 41:5020-5036 (1998).

Hladon, et al. "In Vitro Cytostatic Activity of Some Amino Acid 4-N-Substituted Cytosines" *Archivum Immun. Therap. Experi.* 40:145-150 (1992).

Hoffman, et al. "N-Pyrimidinylamino Acids. III.N (oxopyrimidinyl) derivatives of Neutral Amino Acids" *Z Chem.* 12(1):21-22 (1972) (English abstract).

Houev, et al. "Chiral Tetraalkylmethanes. Two Syntheses of Optically Active Butylethylmethylpropylmethane of Known and High Optical Purity" *J. Org. Chem.* 45:2754-2763 (1980).

Jaeger, et al. "Peptidsynthesen mit-o-Carbamoyl-tyrosin Derivaten" *Chem. Ber.* 101:2762-2770 (1968) (English abstract).

Balaban, Isidore "An Investigation into the Formation of 4(5)-Aminoglyoxalines" *J. Chem. Soc.* Part 1:1-268-273 (1930).

Keszthelyi, et al. "Evidence for a prolonged role of $\alpha_4$integrin throughout active experimental allergic encephalomyelitis" Neurology 47:1053-1059.

Korom, et al. "Blockade of Very Late Angigen-4 Integrin Binding to Fibronectin in Allograft Recipients" *Transplantation* 65:854-859 (1998).

Kroneld, et al. "Expression of the Mucosal Lymphocyte Integrin $\alpha^E \beta_7$ and its Ligand E-cadherin in Salivary Glands of Patients with Sjögren's Syndrome" *Scand. J. Rheumatol* 27:215-218 (1998).

Lazer et al. "Benzoxazolamines and Benzothiazolamines: Potent, Enantiselective Inhibitors of Leukotriene Biosynthesis with a Novel Mechanism of Action" *J. Med. Chem* 37:913-923 (1994).

Luque, et al. "Activated Conformations of Very Late Activation Integrins Detected by a Group of Antibodies (HUTS) Specific for a Novel Regulatory Region (355-425) of the Common β1 Chain" *J. Biol. Chem* 271(19) 11067-11075 (1966).

Ma et al. "Accelerating Effect Induced by the Structure of α-Amino Acid in the Copper-Catalyzed Coupling Reaction of Aryl Halides with α-Amino Acids. Synthesis of Benzolactam-V8" *J. Am. Chem. Soc.* 120:12459-12467 (1998).

Ohta et al. "Emeheterone: Synthesis and Structural Revision" *Heterocycles* 31(9) 1655-1662 (1990).

Ohta et al. "Conversion of 2,5-Diphenyl- and 2,5-Dibenzyl-pyrazines to 2,5-Diketopiperazines" *Chem. Pharm. Bull* 27(12):2980-2987 (1979).

Orosz et al. "Promotion of Experimental Liver Metastasis by Tumor Necrosis Factor" *Int. J. Cancer* 60:867-871 (1995).

Palmer et al. "Sequence and tissue Distribution of the Integrin α9 Subunit, a Novel Partner of β1 That Is Widely Distributed in Epithelia and Muscle" *J. Cell Biol.* 123(5) 1289-1297 (1993).

Pang, et al. "UP-Regulation of αEβ7, A Novel Integrin Adhesion Molecule, on T Cells from Systemic Lupis Erythematosus Patients with Specific Epithelial Involvememnt" *Arthritis & Reumatism* 41(8):1456-1463 (1998).

Papaioannou, et al. Facile Preparation of the 1-Hydorxybenzotriazolyl Ester of N-Tritypyroglutamic Acid and its Application to the Synthesis of TRH, [D-His[2]TRH and Analogues Incorporating *cis*- and *trans*-4-Hydroxy-L-proline: *Acta Chemica Scand.* 49:103-114 (1995).

Paul et al. "Anti-integrin (LFA-1, VLA-4, and Mac-1) antibody treatment and acute cardiac graft rejection in the rat" *Transpl. Int.* 9:420-425 (1996).

Zhu et al. "The Direct Formation of Functionalized Alkyl (aryl)zinc Halides by Oxidative Addition of Highly Reactive Zinc with Organic Halides and Their Reactions with Acid Chlorides, α,β-Unsaturated Ketones, and Allylic, Aryl, and Vinyl Halides" *J. Org. Chem.* 5:1445-1453 (1991).

Schegel, et al. "Inhibition of T Cell Costimulation by VCAM-1 revents Murine Graft-Versus-Host Disease Across Minor Histocompatibility Barriers" *J. Immunol.* 155:3856-3865 (1995).

Simchowitz, et al. "Polyvalent Cations Inhibit Human Neutrophil Chemotaxis by Interfering with the Polymerization of Actin" *J. Biol. Chem* 265(23)13457-13463 (1990).

Sonnenberg, A. "Integrins and Their Ligands" *Current Topics in Microbiology and Immunology* 184:7-35 (1993).

Springer, T.A. "Traffic Signals for Lymphocyte Recirculation and Leukocyte Emigration: The Multistep Paradigm" *Cell* 76:301-314 (1994).

Teranishi, et al. "Synthesis and Chemiluminescence of Coelenterazine (*Oplophorus* Luciferin) Analogues" *Bull. Chem. Soc. Jpn.* 63:3132-3140 (1990).

Verhoef, et al. "Transport of peptide and protein drugs across biological membranes" *Eur. J. Drug Metab. Pharmacokietics* 15(2):83-93 (1990).

Wen, et al. "The Chemistry of 1,2,5,-Thiadiazoles. II. 3,4-Disubstituted Derivatives of 1,2,5-Thiadiazole 1,1-Dioxide" *J. Org. Chem.* 40(19):2743-2748 (1975).

Wen, et al. "1,2,5-Thiadiazolid-3,4-Dione-1-Oxide" *Org. Prep. Proceed.* 1(4):255-258 (1969).

Whittaker, N. "A New Synthesis and the Chemical Properties of 5-Aminopyrimidine" *Chem. Society* 354:1565-1570 (1951).

Yang et al. "Prolongation of Rat Islet Allograft Survival by Treatment with Monoclonal Antibodies Against VLA-4 and LFA-1" *Transplantation* 60:71-76 (1995).

Yednock et al. "$\alpha_4 \beta_1$ Integrin-dependent Cell Adhesion Is Regulated by a Low Affinity Receptor Pool That Is Conformationally Responsive to Ligand" *J. Biol. Chem.*, 270: 28740 (1965).

Yokosaki, et al. "The Integrin $\alpha 9\beta 1$ Mediates Cell Attachment to a Non-RGD Site in the Third Fibronection Type III Repeat of Tenascin" *J. Biol. Chem.* 269:26691-26696.

Tarkowski et al. *Int. Arch. Allergy Immunol* 121(1)25-33 (2000).

* cited by examiner

US 7,026,328 B2

HETEROCYCLIC COMPOUNDS WHICH INHIBIT LEUKOCYTE ADHESION MEDIATED BY $\alpha_4$ INTEGRINS

REFERENCES TO RELATED APPLICATIONS

This application claims the benefit of U.S. Provisional Application 60/383,020, filed May 24, 2002, which is hereby incorporated by reference in its entirety.

BACKGROUND OF THE INVENTION

Field of the Invention

This invention relates to compounds which inhibit leukocyte adhesion and, in particular, leukocyte adhesion mediated by $\alpha_4$ integrins where the $\alpha_4$ integrin is preferably VLA-4.

REFERENCES

The following publications, patents and patent applications are cited in this application as superscript numbers:

[1] Hemler and Takada, European Patent Application Publication No. 330,506, published Aug. 30, 1989
[2] Elices, et al., Cell, 60:577–584 (1990)
[3] Springer, Nature, 346:425–434 (1990)
[4] Osborne, Cell, 62:3–6 (1990)
[5] Vedder, et al., Surgery, 106:509 (1989)
[6] Pretolani, et al., J. Exp. Med., 180:795 (1994)
[7] Abraham, et al., J. Clin. Invest., 93:776 (1994)
[8] Mulligan, et al., J. Immunology, 150:2407 (1993)
[9] Cybulsky, et al., Science, 251:788 (1991)
[10] Li, et al., Arterioscler. Thromb., 13:197 (1993)
[11] Sasseville, et al., Am. J. Path., 144:27 (1994)
[12] Yang, et al., Proc. Nat. Acad. Science (USA), 90:10494 (1993)
[13] Burkly, et al., Diabetes, 43:529 (1994)
[14] Baron, et al., J. Clin. Invest., 93:1700 (1994)
[15] Hamann, et al., J. Immunology, 152:3283 (1994)
[16] Yednock, et al., Nature, 356:63 (1992)
[17] Baron, et al., J. Exp. Med., 177:57 (1993)
[18] van Dinther-Janssen, et al., J. Immunology, 147:4207 (1991)
[19] van Dinther-Janssen, et al., Annals. Rheumatic Dis., 52:672 (1993)
[20] Elices, et al., J. Clin. Invest., 93:405 (1994)
[21] Postigo, et al., J. Clin. Invest., 89:1445 (1991)
[22] Paul, et al., Transpl. Proceed., 25:813 (1993)
[23] Okarhara, et al., Can. Res., 54:3233 (1994)
[24] Paavonen, et al., Int. J. Can., 58:298 (1994)
[25] Schadendorf, et al., J. Path., 170:429 (1993)
[26] Bao, et al., Diff., 52:239 (1993)
[27] Lauri, et al., British J. Cancer, 68:862 (1993)
[28] Kawaguchi, et al., Japanese J. Cancer Res., 83:1304 (1992)
[29] Konradi, et al., PCT/US00/01686, filed Jan. 21, 2000.

All of the above publications are herein incorporated by reference in their entirety to the same extent as if each individual publication was specifically and individually indicated to be incorporated by reference in its entirety.

STATE OF THE ART

VLA-4 (also referred to as $\alpha_4\beta_1$ integrin and CD49d/CD29), first identified by Hemler and Takada,[1] is a member of the β1 integrin family of cell surface receptors, each of which comprises two subunits, an α chain and a β chain. VLA-4 contains an α4 chain and a β1 chain. There are at least nine β1 integrins, all sharing the same β1 chain and each having a distinct α chain. These nine receptors all bind a different complement of the various cell matrix molecules, such as fibronectin, laminin, and collagen. VLA-4, for example, binds to fibronectin. VLA-4 also binds non-matrix molecules that are expressed by endothelial and other cells. These non-matrix molecules include VCAM-1, which is expressed on cytokine-activated human umbilical vein endothelial cells in culture. Distinct epitopes of VLA-4 are responsible for the fibronectin and VCAM-1 binding activities and each activity has been shown to be inhibited independently.[2]

Intercellular adhesion mediated by VLA-4 and other cell surface receptors is associated with a number of inflammatory responses. At the site of an injury or other inflammatory stimulus, activated vascular endothelial cells express molecules that are adhesive for leukocytes. The mechanics of leukocyte adhesion to endothelial cells involves, in part, the recognition and binding of cell surface receptors on leukocytes to the corresponding cell surface molecules on endothelial cells. Once bound, the leukocytes migrate across the blood vessel wall to enter the injured site and release chemical mediators to combat infection. For reviews of adhesion receptors of the immune system, see, for example, Springer[3] and Osborn.[4]

Inflammatory brain disorders, such as experimental autoimmune encephalomyelitis (EAE), multiple sclerosis (MS) and meningitis, are examples of central nervous system disorders in which the endothelium/leukocyte adhesion mechanism results in destruction to otherwise healthy brain tissue. Large numbers of leukocytes migrate across the blood brain barrier (BBB) in subjects with these inflammatory diseases. The leukocytes release toxic mediators that cause extensive tissue damage resulting in impaired nerve conduction and paralysis.

In other organ systems, tissue damage also occurs via an adhesion mechanism resulting in migration or activation of leukocytes. For example, it has been shown that the initial insult following myocardial ischemia to heart tissue can be further complicated by leukocyte entry to the injured tissue causing still further insult (Vedder et al.).[5] Other inflammatory or medical conditions mediated by an adhesion mechanism include, by way of example, asthma[6-8], Alzheimer's disease, atherosclerosis,[9-10] AIDS dementia,[11] diabetes[12-14] (including acute juvenile onset diabetes), inflammatory bowel disease[15] (including ulcerative colitis and Crohn's disease), multiple sclerosis,[16-17] rheumatoid arthritis,[18-21] tissue transplantation,[22] tumor metastasis,[23-28] meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

Substituted aminopyrimidines, as a class, have been disclosed as inhibiting binding of VLA-4 to VCAM-1 and, accordingly, exhibit anti-inflammatory properties.[29] While these compounds possess antagonist properties to such binding, enhanced bioavailability of these compounds would augment their efficacy.

SUMMARY OF THE INVENTION

This invention is directed to the discovery that certain N-[2-N',N'-diethylamino-5-aminosulfonylphenylpyrimidin-4-yl]-p-carbomyloxy-phenylalanine compounds possess unexpectedly superior bioavailability, as measured by their AUC, as compared to other substituted aminopyrimidine compounds previously disclosed.

In one of its composition aspects, this invention is directed to a compound of Formula (I):

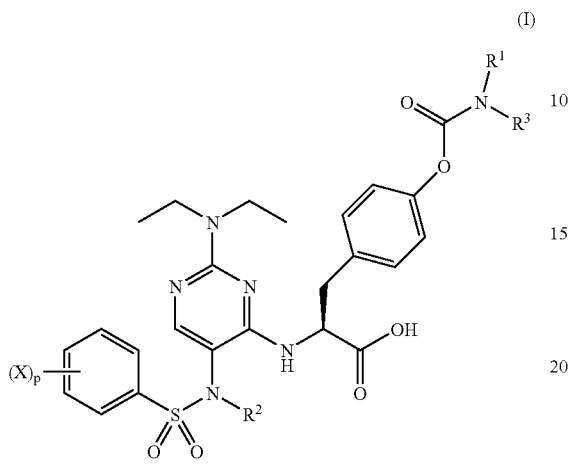

wherein each X is independently fluoro, chloro or bromo;
p is an integer from 0 to 3;
$R^1$ and $R^3$ together with the nitrogen atom to which they are bound form an azetidinyl, pyrrolidinyl, pyrrolyl, 2,5-dihydopyrrol-1-yl, piperidinyl, or 1,2,3,6-tetrahydropyridin-1-yl;
$R^2$ is selected from the group consisting of lower alkyl, lower alkenyl, and lower alkylenecycloalkyl;
and pharmaceutically acceptable salts thereof.

In a preferred embodiment, $R^1$ and $R^3$ together with the nitrogen atom to which they are bound form an azetidinyl, pyrrolidinyl, or piperidinyl group.

In a preferred embodiment, this invention provides compounds of Formula (II):

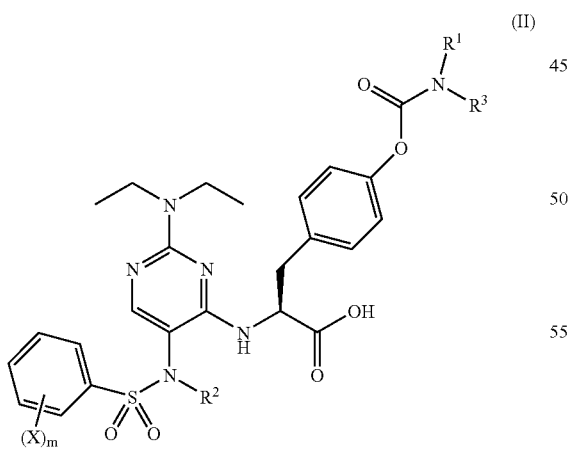

wherein each X is independently selected from the group consisting of fluoro and chloro;
m is an integer equal to 1 or 2;
$R^2$ is selected from the group consisting of lower alkyl, lower alkenyl, and lower alkylenecycloalkyl;
$R^1$ and $R^3$ together with the nitrogen atom to which they are bound form an azetidinyl, pyrrolidinyl, or piperidinyl group;
and pharmaceutically acceptable salts thereof.

In a particularly preferred embodiment, this invention provides compounds of Formula (III)

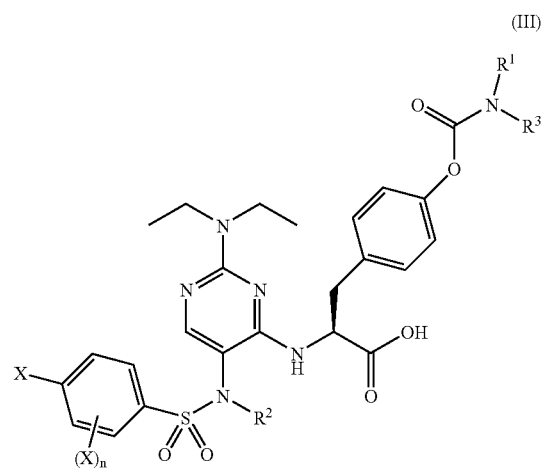

wherein each X is independently fluoro or chloro;
n is zero or one;
$R^2$ is —$CH_2$—R' where R' is selected from the group consisting of hydrogen, methyl or —CH=$CH_2$;
$R^1$ and $R^3$ together with the nitrogen atom to which they are bound form an azetidinyl, pyrrolidinyl, or piperidinyl group;
and pharmaceutically acceptable salts thereof.

In another of its composition aspects, this invention is directed to a compound of Formula (IV):

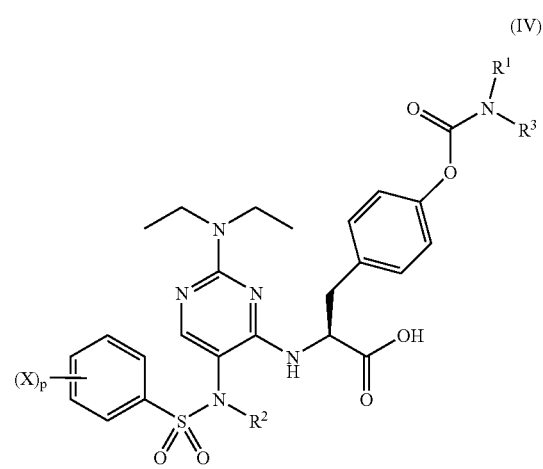

wherein each X is independently fluoro, chloro or bromo;
p is an integer from 0 to 3;
$R^1$ and $R^3$ together with the nitrogen atom to which they are bound form an azetidinyl, pyrrolidinyl, pyrrolyl, 2,5-dihydopyrrol-1-yl, piperidinyl, or 1,2,3,6-tetrahydropyridin-1-yl;
$R^2$ is lower alkynyl;
and pharmaceutically acceptable salts thereof.

In a preferred embodiment, $R^1$ and $R^3$ together with the nitrogen atom to which they are bound form an azetidinyl, pyrrolidinyl, or piperidinyl group and $R^2$ is propargyl.

In a preferred embodiment, this invention provides compounds of Formula (V):

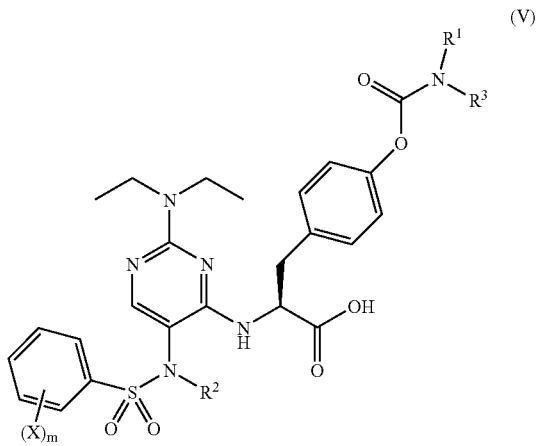

(V)

wherein each X is independently selected from the group consisting of fluoro and chloro;
m is an integer equal to 1 or 2;
$R^2$ is lower alkynyl;
$R^1$ and $R^3$ together with the nitrogen atom to which they are bound form an azetidinyl, pyrrolidinyl, or piperidinyl group;
and pharmaceutically acceptable salts thereof.

In a particularly preferred embodiment, this invention provides compounds of Formula (VI)

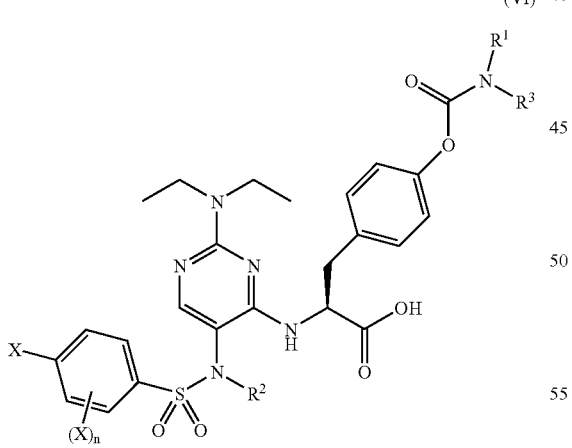

(VI)

wherein each X is independently fluoro or chloro;
n is zero or one;
$R^2$ is lower alkynyl;
$R^1$ and $R^3$ together with the nitrogen atom to which they are bound form an azetidinyl, pyrrolidinyl, or piperidinyl group;
and pharmaceutically acceptable salts thereof.

N-[2-N',N'-diethylamino-5-aminosulfonylphenylpyrimidin-4-yl]-p-carbomyloxy-phenylalanine compounds within the scope of this invention include those set forth in Table I as follows:

TABLE I

| $R^1$ and $R^3$ | $R^2$ | $(X)_p$ | Cmpd No. |
|---|---|---|---|
| pyrrolidinyl | ethyl | 4-fluorophenyl | 2 |
| pyrrolidinyl | methyl | 4-fluorophenyl | 3 |
| pyrrolidinyl | methyl | 4-chlorophenyl | 4 |
| pyrrolidinyl | ethyl | 4-chlorophenyl | 1 |
| piperidinyl | methyl | 4-fluorophenyl | 5 |
| azetidinyl | ethyl | 4-fluorophenyl | 7 |
| azetidinyl | methyl | 4-fluorophenyl | 8 |
| azetidinyl | methyl | 4-chlorophenyl | 9 |
| azetidinyl | ethyl | 4-chlorophenyl | 10 |
| piperidinyl | ethyl | 4-fluorophenyl | 6 |
| azetidinyl | ethyl | 2,4-difluorophenyl | 14 |
| pyrrolidinyl | methyl | 2,4-difluorophenyl | 11 |
| pyrrolidinyl | ethyl | 2,4-difluorophenyl | 12 |
| azetidinyl | methyl | 2,4-difluorophenyl | 13 |
| pyrrolidinyl | propargyl | 4-fluorophenyl | 15 |
| pyrrolidinyl | progargyl | 2,4-difluorophenyl | 16 |
| azetidinyl | propargyl | 2,4-difluorophenyl | 17 |
| azetidinyl | propargyl | 4-fluorophenyl | 18 |
| pyrrolidinyl | progargyl | 4-chlorophenyl | 19 |

Specific compounds within the scope of this invention include the following compounds. As used below, these compounds are named based on phenylalanine derivatives but, alternatively, these compounds could have been named based on N-[2-N',N'-diethylamino-5-aminosulfonylphenyl-pyrimidin-4-yl]-p-carbomyloxyphenylalanine derivatives or 2-{2-diethylamino-5-[(benzenesulfonyl)methylamino]-pyrimidin-4-ylamino}-p-carbamoyloxy-phenyl)propionic acid derivatives.

N-(2-[N',N'-diethylamino]-5-[N'''-(4-chlorophenylsulfonyl)-N'''-ethylamino]pyrimidin-4-yl)-4'-(pyrrolidin-1-ylcarbonyloxy)-L-phenylalanine;

N-(2-[N',N'-diethylamino]-5-[N'''-(4-fluorophenylsulfonyl)-N'''-ethylamino]pyrimidin-4-yl)-4'-(pyrrolidin-1-ylcarbonyloxy)-L-phenylalanine;

N-(2-[N',N'-diethylamino]-5-[N'''-(4-fluorophenylsulfonyl)-N'''-methylamino]pyrimidin-4-yl)-4'-(pyrrolidin-1-ylcarbonyloxy)-L-phenylalanine;

N-(2-[N',N'-diethylamino]-5-[N'''-(4-chlorophenylsulfonyl)-N'''-methylamino]pyrimidin-4-yl)-4'-(pyrrolidin-1-ylcarbonyloxy)-L-phenylalanine;

N-(2-[N',N'-diethylamino]-5-[N"-(4-fluorophenylsulfonyl)-N"-methylamino]pyrimidin-4-yl)-4'-(piperidin-1-ylcarbonyloxy)-L-phenylalanine;

N-(2-[N',N'-diethylamino]-5-[N"-(4-fluorophenylsulfonyl)-N"-ethylamino]pyrimidin-4-yl)-4'-(piperidin-1-ylcarbonyloxy)-L-phenylalanine;

N-(2-[N',N'-diethylamino]-5-[N"-(4-fluorophenylsulfonyl)-N"-ethylamino]pyrimidin-4-yl)-4'-(azetidin-1-ylcarbonyloxy)-L-phenylalanine;

N-(2-[N',N'-diethylamino]-5-[N"-(4-fluorophenylsulfonyl)-N"-methylamino]pyrimidin-4-yl)-4'-(azetidin-1-ylcarbonyloxy)-L-phenylalanine;

N-(2-[N',N'-diethylamino]-5-[N"-(4-chlorophenylsulfonyl)-N"-methylamino]pyrimidin-4-yl)-4'-(azetidin-1-ylcarbonyloxy)-L-phenylalanine;

N-(2-[N',N'-diethylamino]-5-[N"-(4-chlorophenylsulfonyl)-N"-ethylamino]pyrimidin-4-yl)-4'-(azetidin-1-ylcarbonyloxy)-L-phenylalanine;

N-(2-[N',N'-diethylamino]-5-[N"-(2,4-difluorophenylsulfonyl)-N"-methylamino]pyrimidin-4-yl)-4'-(pyrrolidin-1-ylcarbonyloxy)-L-phenylalanine;

N-(2-[N',N'-diethylamino]-5-[N"-(2,4-difluorophenylsulfonyl)-N"-ethylamino]pyrimidin-4-yl)-4'-(pyrrolidin-1-ylcarbonyloxy)-L-phenylalanine;

N-(2-[N',N'-diethylamino]-5-[N"-(2,4-difluorophenylsulfonyl)-N"-methylamino]pyrimidin-4-yl)-4'-(azetidin-1-ylcarbonyloxy)-L-phenylalanine;

N-(2-[N',N'-diethylamino]-5-[N"-(2,4-difluorophenylsulfonyl)-N"-ethylamino]pyrimidin-4-yl)-4'-(azetidin-1-ylcarbonyloxy)-L-phenylalanine;

N-(2-[N',N'-diethylamino]-5-[N"-(4-fluorophenylsulfonyl)-N"-propargylamino]pyrimidin-4-yl)-4'-(pyrrolidin-1-ylcarbonyloxy)-L-phenylalanine;

N-(2-[N',N'-diethylamino]-5-[N"-(2,4-difluorophenylsulfonyl)-N"-propargylamino]pyrimidin-4-yl)-4'-(pyrrolidin-1-ylcarbonyloxy)-L-phenylalanine;

N-(2-[N',N'-diethylamino]-5-[N"-(2,4-difluorophenylsulfonyl)-N"-propargylamino]pyrimidin-4-yl)-4'-(azetidin-1-ylcarbonyloxy)-L-phenylalanine;

N-(2-[N',N'-diethylamino]-5-[N"-(4-fluorophenylsulfonyl)-N"-propargylamino]pyrimidin-4-yl)-4'-(azetidin-1-ylcarbonyloxy)-L-phenylalanine;

N-(2-[N',N'-diethylamino]-5-[N"-(4-chlorophenylsulfonyl)-N"-propargylamino]pyrimidin-4-yl)-4'-(pyrrolidin-1-ylcarbonyloxy)-L-phenylalanine; and pharmaceutically acceptable salts thereof.

In another aspect, this invention provides pharmaceutical compositions comprising a pharmaceutically acceptable carrier and a therapeutically effective amount of the compounds defined herein.

In one of its method aspects, this invention is directed to a method for treating a disease mediated at least in part by $\alpha_4$ integrins, preferably VLA-4, in a patient, which method comprises administering a pharmaceutical composition comprising a pharmaceutically acceptable carrier and a therapeutically effective amount of a compound of this invention.

The compounds and pharmaceutical compositions of this invention are useful for treating disease conditions mediated at least in part by $\alpha_4$ integrins, preferably VLA-4, or leucocyte adhesion. Such disease conditions include, by way of example, asthma, Alzheimer's disease, atherosclerosis, AIDS dementia, diabetes (including acute juvenile onset diabetes), inflammatory bowel disease (including ulcerative colitis and Crohn's disease), multiple sclerosis, rheumatoid arthritis, tissue transplantation, tumor metastasis, meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

Other disease conditions include, but are not limited to, inflammatory conditions such as erythema nodosum, allergic conjunctivitis, optic neuritis, uveitis, allergic rhinitis, Ankylosing spondylitis, psoriatic arthritis, vasculitis, Reiter's syndrome, systemic lupus erythematosus, progressive systemic sclerosis, polymyositis, dermatomyositis, Wegner's granulomatosis, aortitis, sarcoidosis, lymphocytopenia, temporal arteritis, pericarditis, myocarditis, congestive heart failure, polyarteritis nodosa, hypersensitivity syndromes, allergy, hypereosinophilic syndromes, Churg-Strauss syndrome, chronic obstructive pulmonary disease, hypersensitivity pneumonitis, chronic active hepatitis, interstitial cystitis, autoimmune endocrine failure, primary biliary cirrhosis, autoimmune aplastic anemia, chronic persistent hepatitis and thyroiditis.

In a preferred embodiment, the disease condition is an inflammatory disease.

DETAILED DESCRIPTION OF THE INVENTION

As above, this invention relates to compounds which inhibit leukocyte adhesion and, in particular, leukocyte adhesion mediated at least in part by $\alpha_4$ integrins, preferably VLA-4. However, prior to describing this invention in further detail, the following terms will first be defined.

Definitions

Unless otherwise stated, the following terms used in the specification and claims have the meanings given below:

As used herein, "lower alkyl" refers to monovalent alkyl groups having from 1 to 5 carbon atoms including straight and branched chain alkyl groups. This term is exemplified by groups such as methyl, ethyl, iso-propyl, n-propyl, n-butyl, iso-butyl, sec-butyl, t-butyl, n-pentyl and the like.

The term "lower alkylene" refers to divalent alkylene groups of from 1 to 4 carbon atoms including straight and branched chain alkylene groups. This term is exemplified by groups such as methylene, ethylene, n-propylene, iso-propylene (—CH$_2$CH(CH$_3$)— and —CH(CH$_3$)CH$_2$—) and the like.

The term "lower alkenyl" refers to an alkenyl group preferably having from 2 to 6 carbon atoms and having at least 1 site and preferably only 1 site of alkenyl unsaturation (i.e., >C═C<). This term is exemplified by groups such as allyl, ethenyl, propenyl, butenyl, and the like.

The term "lower alkynyl" refers to an alkynyl group preferably having from 2 to 6 carbon atoms and having at least 1 site and preferably only 1 site of alkynyl unsaturation (i.e., —C≡C—). This term is exemplified by groups such as acetyl (—C≡CH), propargyl (—CH$_2$—C≡CH), 3-butynyl (—CH$_2$CH$_2$C≡CH$_3$) and the like.

The term "lower cycloalkyl" refers to cyclic alkyl groups of from 3 to 6 carbon atoms having a single cyclic ring including, by way of example, cyclopropyl, cyclobutyl, cyclopentyl and cyclohexyl.

The term "lower alkylenecycloalkyl" refers to the group consisting of a lower alkylene-lower cycloalkyl, as defined herein. Such groups are exemplified by methylenecyclopropyl (—CH$_2$-cyclopropyl), ethylenecyclopropyl and the like.

"Pharmaceutically acceptable carrier" means a carrier that is useful in preparing a pharmaceutical composition that is generally safe, non-toxic and neither biologically nor otherwise undesirable, and includes a carrier that is acceptable for veterinary use as well as human pharmaceutical use. "A pharmaceutically acceptable carrier" as used in the specification and claims includes both one and more than one such carrier.

"Treating" or "treatment" of a disease includes:
(1) preventing the disease, i.e., causing the clinical symptoms of the disease not to develop in a mammal that may be exposed to or predisposed to the disease but does not yet experience or display symptoms of the disease,
(2) inhibiting the disease, i.e., arresting or reducing the development of the disease or its clinical symptoms, or
(3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Pharmaceutically acceptable salt" refers to pharmaceutically acceptable salts of a compound of Formula I which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

Integrins are a large family of homologous transmembrane linker proteins that are the principal receptors on animal cells for binding most extracellular matrix proteins, such as collagen, fibronectin, and laminin. The integrins are heterodimers comprised of an α chain and a β chain. To date, twenty different integrin heterodimers, made from 9 different α subunits and 14 different β subunits, have been identified. The term "$\alpha_4$ integrins" refers to the class of heterodimer, enzyme-linked cell-surface receptors that contain the $\alpha_4$ subunit paired with any of the β subunits. VLA-4 is an example of an $\alpha_4$ integrin, and is a heterodimer of the $\alpha_4$ and $\beta_1$ subunits, and is also referred to as $\alpha_4\beta_1$ integrin.

Compound Preparation

The compounds of this invention can be prepared from readily available starting materials using the methods and procedures set forth in the examples below. These methods and procedures outline specific reaction protocols for preparing N-[2-N',N'-diethylamino-5-aminosulfonylphenylyrimidin-4-yl]-p-carbomyloxy-phenylalanine compounds. Compounds within the scope not exemplified in these examples and methods are readily prepared by appropriate substitution of starting materials which are either commercially available or well known in the art.

Other procedures and reaction conditions for preparing the compounds of this invention are described in the examples set forth below. Additionally, other procedures for preparing compounds useful in certain aspects of this invention are disclosed in U.S. Pat. No. 6,492,372, issued Dec. 10, 2002; the disclosure of which is incorporated herein by reference in its entirety.

Pharmaceutical Formulations

When employed as pharmaceuticals, the compounds of this invention are usually administered in the form of pharmaceutical compositions. These compositions can be administered by a variety of routes including oral, rectal, transdermal, subcutaneous, intravenous, intramuscular, and intranasal. These compositions are effective by both injectable and oral delivery. Such compositions are prepared in a manner well known in the pharmaceutical art and comprise at least one active compound.

This invention also includes pharmaceutical compositions which contain, as the active ingredient, one or more of the compounds of Formula I above associated with pharmaceutically acceptable carriers. In making the compositions of this invention, the active ingredient is usually mixed with an excipient, diluted by an excipient or enclosed within such a carrier which can be in the form of a capsule, sachet, paper or other container. The excipient employed is typically an excipient suitable for administration to human subjects or other mammals. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

The following formulation examples illustrate the pharmaceutical compositions of the present invention.

FORMULATION EXAMPLE 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
| --- | --- |
| Active Ingredient | 5 |
| Lactose | 95 |

The active mixture is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

FORMULATION EXAMPLE 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
|---|---|
| Active Ingredient | 25 mg |
| Saturated fatty acid glycerides | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 ml dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425 mg quantities.

FORMULATION EXAMPLE 9

An intravenous formulation may be prepared as follows:

| Ingredient | Quantity |
|---|---|
| Active Ingredient | 250.0 mg |
| Isotonic saline | 1000 ml |

FORMULATION EXAMPLE 10

A topical formulation may be prepared as follows:

| Ingredient | Quantity |
|---|---|
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Direct or indirect placement techniques may be used when it is desirable or necessary to introduce the pharmaceutical composition to the brain. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Utility

The compounds of this invention inhibit, in vivo, adhesion of leukocytes to endothelial cells mediated at least in part by $\alpha_4$ integrins, preferably VLA-4, by competitive binding to $\alpha_4$ integrins, preferably VLA-4. Accordingly, the compounds of this invention can be used in the treatment of mammalian diseases mediated at least in part by $\alpha_4$ integrins, preferably VLA-4, or leucocyte adhesion. Such diseases include inflammatory diseases in mammalian patients such as asthma, Alzheimer's disease, atherosclerosis, AIDS dementia, diabetes (including acute juvenile onset diabetes), inflammatory bowel disease (including ulcerative colitis and Crohn's disease), multiple sclerosis, rheumatoid arthritis, tissue transplantation, tumor metastasis, meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

The amount administered to the mammalian patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically effective dose." Amounts effective for this use will depend on the disease condition being treated as well as by the judgment of the attending clinician depending upon factors such as the severity of the inflammation, the age, weight and general condition of the patient, and the like.

The compositions administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention will vary according to, for example, the particular use for which the treatment is made, the manner of administration of the compound, the health and condition of the patient, and the judgment of the prescribing physician. For example, for intravenous administration, the dose will typically be in the range of about 20 μg to about 500 μg per kilogram body weight, preferably about 100 μg to about 300 μg per kilogram body weight. Suitable dosage ranges for intranasal administration are generally about 0.1 pg to 1 mg per kilogram body weight. Effective doses can be extrapolated from dose-response curves derived from in vitro or animal model test systems.

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

| | |
|---|---|
| AUC = | Area under the curve |
| bd = | broad doublet |
| bs = | broad singlet |
| BSA = | bovine serum albumin |
| d = | doublet |
| DMAP = | 4-N,N-dimethylaminopyridine ethylcarbodiimide hydrochloride |
| EDTA = | Ethylenediamine tetraacetic acid |
| EtOAc = | ethyl acetate |
| EtOH = | ethanol |
| eq. = | equivalent |
| FACS = | Fluorescence activated Cell Sorter |
| FITC = | Fluorescein isothiocyanate |
| g = | grams |
| i.p. = | intraperitoneal |
| h = | hour |
| HBSS = | Hank's Balanced Saline Solution |
| Hct = | hematocrit, or measurement of packed red blood cells obtained by centrifugation in a volume of a blood sample |
| HB or Hb = | hemoglobin |
| HEPES = | 4-(2-hydroxyethyl)-1-piperazine-ethanesulfonic acid |
| IgG Fc = | a binding domain of the immunoglobulin |
| kg = | killogram |
| L = | liter |
| m = | multiplet (when used with NMR data) |
| M = | Molar |
| MCH = | Mean Corpusular Hemoglobin; Hb/RBC |
| MCHC = | mean corpuscular hemoglobin count expressed as a percentage; Hb/Hct. |
| MCV = | mean corpuscular volume; the avg. volume of erythrocytes, conventionally expressed in cubic micrometers per red cell. |
| MeOH = | methanol |
| mg = | milligram |
| mL = | milliliter |
| mm = | millimeter |
| mM = | millimolar |
| mol = | moles |
| mmol = | millimol |
| mpk = | milligrams per killogram |
| N = | normal |
| ng = | nanograms |
| PBS++ = | Phosphate buffered saline |
| psi = | pounds per square inch |
| q.s. or Q.S. = | bring to volume |
| Rfs or $R_f$ = | retention factor |
| rpm = | rotations per minute |
| rt or RT = | room temperature |
| s = | singlet |
| t = | triplet |
| TFA = | trifluoroacetic acid |
| THF = | tetrahydrofuran |
| TLC or tlc = | thin layer chromatography |
| μL = | microliter |
| μg = | microgram |
| μm = | microns |
| $V_t$ = | Total volume |
| WBC = | White Blood Cells |
| w/v = | weight to volume |

Compounds of the present invention may be prepared as illustrated in Scheme 1 and as described in the methods below:
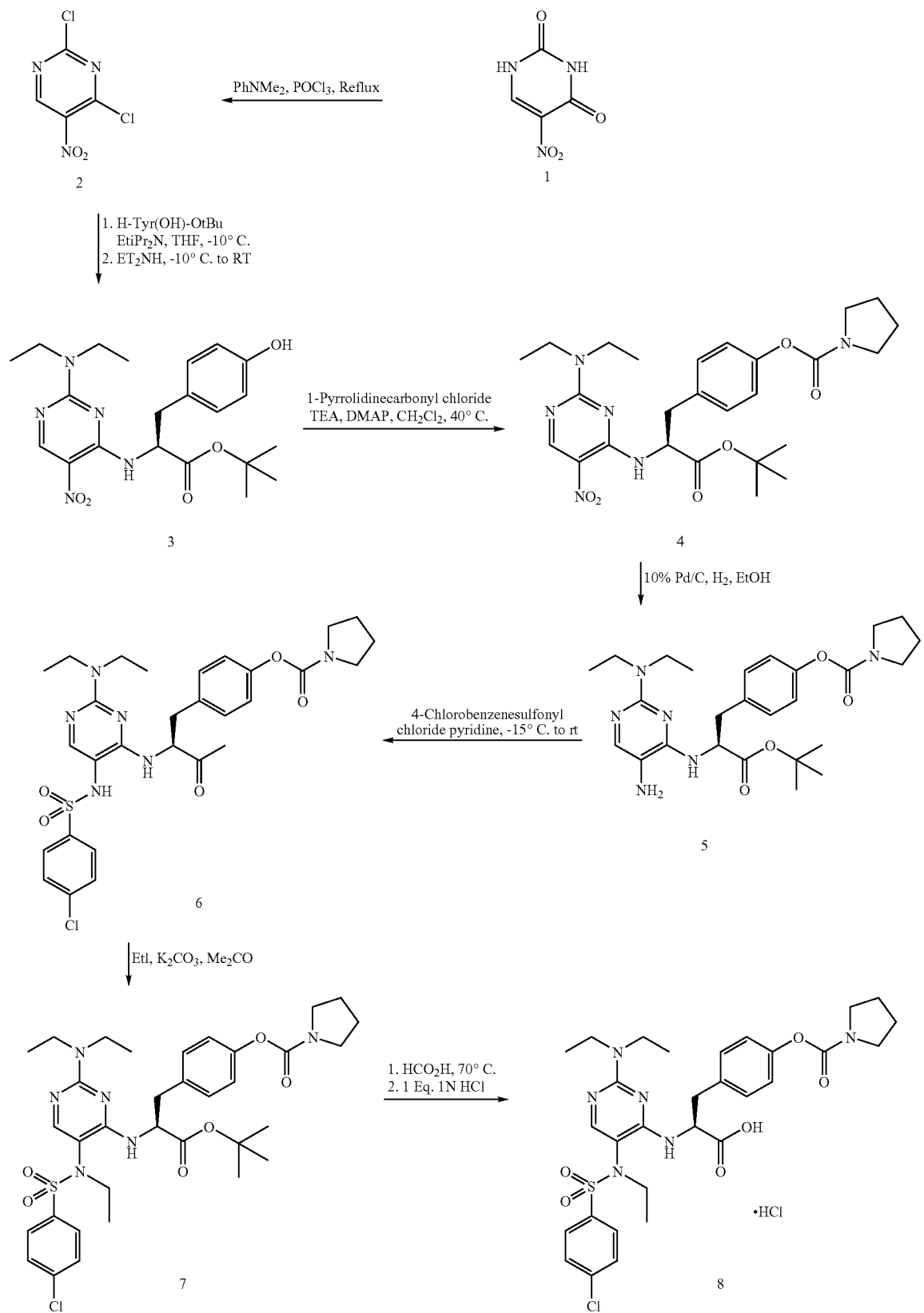

Example 1

Preparation of N-(2-[N',N'-diethylamino]-5-[N"-(4-chlorophenylsulfonyl)-N"-ethylamino]pyrimidin-4-yl)-4'-(pyrrolidin-1-ylcarbonyloxy)-L-phenylalanine Step 1: Preparation of 2,4-Dichloro-5-nitropyrimidine (2). 5-Nitrouracil, (1), was treated with phosphorous oxychloride ($POCl_3$) and N,N-dimethylaniline ($PhNMe_2$), according to the procedure of Whittaker (J. Chem. Soc. 1951, 1565), to give compound 2. Compound 2 is also available from City Chemical (West Haven, Conn.).

Step 2: Preparation of N-(2-[N',N'-diethylamino]-5-nitropyrimidin-4-yl)-L-tyrosine tert-butyl ester (3). To a solution of L-tyrosine tert-butyl ester (H-Tyr(OH)-OtBu) (30.6 g, 0.129 mol) in THF (250 mL) at −10° C. was added 2,4-dichloro-5-nitropyrimidine (25 g, 0.129 mol), keeping the temperature below 5° C. during the addition. Once the addition was complete, N,N-diisopropylethylamine ($EtiPr_2N$) (33.7 mL, 0.194 mol) was added dropwise. After stirring for 1 h at −10° C., diethylamine ($Et_2NH$) (66.73 mL, 0.645 mol) was added slowly, and then the reaction mixture was warmed to room temperature overnight. The reaction mixture was diluted with diethyl ether (500 mL), and the organic layer was washed with 0.2 N citric acid (3×150 mL), water (1×150 mL), and 10% $K_2CO_3$ (3×150 mL). The organic phase was dried ($Na_2SO_4$), filtered, and concentrated in vacuo to yield a yellow residue. The residue was purified by flash chromatography (20% EtOAc/hexanes on silica gel) to yield 37.39 g (67%) of compound 3 as a yellow foam. $R_f$=0.21 (25% EtOAc/hexanes on silica gel).

Step 3: Preparation of N-(2-[N',N'-diethylamino]-5-nitropyrimidin-4-yl)-4'-(pyrrolidin-1-ylcarbonyloxy)-L-phenylalanine tert-butyl ester (4). To a solution of N-(2-[N',N'-diethylamino]-5-nitropyrimidin-4-yl)-L-tyrosine tert-butyl ester (37.39 g, 0.087 mol) in $CH_2Cl_2$ (150 mL) was added DMAP (10.59 g, 0.087 mol). After 5 minutes triethylamine (TEA) (18.19 mL, 0.131 mol) was added dropwise. 1-Pyrrolidinecarbamoyl chloride (14.42 mL, 0.131 mol) was added dropwise, and the reaction was heated to reflux (40° C.) overnight. The reaction mixture was concentrated in vacuo and taken up in EtOAc (300 mL). The organic phase was washed with 0.2 N citric acid (3×150 mL), water (1×150 mL), sat. $NaHCO_3$ (3×150 mL), brine (1×150 mL), dried ($Na_2SO_4$), filtered, and concentrated in vacuo to yield 43.07 g (94%) of compound 4 as a yellow solid. $R_f$=0.5 (50% EtOAc/hexanes on silica gel).

Step 4: Preparation of N-(2-[N',N'-diethylamino]-5-aminopyrimidin-4-yl)-4'-(pyrrolidin-1-ylcarbonyloxy)-L-phenylalanine tert-butyl ester (5). A mixture of N-(2-[N',N'-diethylamino]-5-nitropyrimidin-4-yl)-4'-(pyrrolidin-1-ylcarbonyloxy)-L-phenylalanine tert-butyl ester (43.07 g, 0.081 mol) and 10% Pd/C (4.3 g, 10 wt % Pd) in EtOH (200 mL) was shaken under 45 psi hydrogen until TLC (50% EtOAc/hexanes on silica gel) showed 100% conversion to product (48 hours). The reaction mixture was then filtered through a Celite plug and concentrated in vacuo to yield 40.29 g (100%) of compound 5 as a purple foam. $R_f$=0.11 (6:1 EtOAc/hexanes on silica gel).

Step 5: Preparation of N-(2-[N',N'-diethylamino]-5-[N"-(4-chlorophenyl-sulfonyl)amino]pyrimidin-4-yl)-4'-(pyrrolidin-1-ylcarbonyloxy)-L-phenylalanine tert-butyl ester (6). A pyridine (160 mL) solution of N-(2-[N',N'-diethylamino]-5-aminopyrimidin-4-yl)-4'-(pyrrolidin-1-ylcarbonyloxy)-L-phenylalanine tert-butyl ester (40.29 g, 0.081 mol) was cooled to −20° C. with a dry ice/$CH_3CN$ bath. The mixture stirred for 30 minutes, and then 4-chlorobenzenesulfonyl chloride (17.06 g, 0.081 mol) was added slowly. The reaction was stirred at −20° C. to −15° C. for 4 h and then allowed to warm to room temperature overnight. The reaction was diluted with EtOAc (400 mL), and the organic phase was washed with 0.2 N citric acid (3×150 mL), water (1×150 mL), sat. $NaHCO_3$ (3×150 mL), brine (1×150 mL), dried ($Na_2SO_4$), filtered, and concentrated in vacuo to yield a brown residue. The residue was purified by flash chromatography (50% EtOAc/hexanes on silica gel) to yield 43.49 g (80%) of compound 6 as a yellow foam. $R_f$=0.35 (50% EtOAc/hexanes on silica gel).

Step 6: Preparation of N-(2-[N',N'-diethylamino]-5-[N"-(4-chlorophenyl-sulfonyl)-N"-ethylaminol]pyrimidin-4-yl)-4'-(pyrrolidin-1-ylcarbonyloxy)-L-phenylalanine tert-butyl ester (7). To a solution of N-(2-[N',N'-diethylamino]-5-[N"-(4-chlorophenyl-sulfonyl)amino]pyrimidin-4-yl)-4'-(pyrrolidin-1-ylcarbonyloxy)-L-phenylalanine tert-butyl ester (42.92 g, 0.064 mol) in acetone ($Me_2CO$) (600 mL) was added $K_2CO_3$ (12.75 g, 0.096 mol), and the mixture was stirred for 1 h at room temperature. Iodoethane (EtI) (7.73 mL, 0.096 mol) was then added slowly, and the reaction mixture was stirred overnight at room temperature. The reaction mixture was concentrated in vacuo, and the residue was taken tip in EtOAc (300 mL). The organic phase was washed with water (2×300 mL), brine (1×100 mL), dried ($Na_2SO_4$), filtered, and concentrated in vacuo. The residue was purified by flash chromatography (2:1 hexanes/EtOAc on silica gel) to yield 37.36 g (85%) of compound 7 as a white solid. $R_f$0.53 (50% EtOAc/hexanes on silica gel).

Step 7: Preparation of N-(2-[N',N'-diethylamino]-5-[N"-(4-chlorophenylsulfonyl)-N"-ethylamino]pyrimidin-4-yl)-4'-(pyrrolidin-1-ylcarbonyloxy)-L-phenylalanine hydrochloride (8). A formic acid (500 mL) solution of N-(2-[N',N'-diethylamino]-5-[N"-(4-chlorophenyl-sulfonyl)-N"-ethylamino]pyrimidin-4-yl)-4'-(pyrrolidin-1-ylcarbonyloxy)-L-phenylalanine tert-butyl ester (36.21 g, 0.052 mol) was heated to 70° C. for 2 h and then concentrated in vacuo. The residue was dissolved again in formic acid (500 mL) and heated again at 70° C. for 2 h. The solution was reduced in volume by 80% and then treated with at least 1 eq. of 1.0 N HCl (52 mL, 0.052 mol) followed by distilled water (100 mL). The resulting heterogeneous mixture was concentrated in vacuo. Distilled water (100 mL) was added, and the heterogeneous mixture was concentrated in vacuo. The latter steps were repeated twice to yield a wet white product. This was dried by placing under high vacuum at 40° C. (7 days) to yield 32.8 g (93%) of compound 8, as a free-flowing white solid. $R_f$0.25 (7/3 MeOH/$H_2O$+0.1% TFA, reverse phase).

$^1$H NMR ($CD_3OD$) δ 8.22 (bs, 1H), 7.82–7.79 (m, 1H), 7.64–7.60 (m, 2H), 7.36–7.33 (m, 1H), 7.22–7.13 (m, 2H), 7.07–6.98 (m, 2H), 4.91–4.90 (m, 1H), 4.80–4.79 (m, 1H), 4.12–4.10 (m, 1H), 3.87–3.75 (m, 1H), 3.55–3.53 (m, 4H), 3.41–3.40 (m, 3H), 3.26–3.19 (m, 2H), 2.03 (bs, 1H), 1.97–1.89 (m, 3H), 1.27–1.15 (m, 6H), 1.10–1.05 (t, 1.5H), 0.97–0.92 (t, 1.5H) $^{13}$C NMR ($CD_3OD$) δ 175.8, 175.7, 166.5, 162.7, 162.2, 155.8, 155.7, 155.7, 152.6, 148.1, 147.7, 142.0, 138.5, 136.2, 132.6, 132.3, 131.9, 131.7, 123.7, 111.8, 111.5, 62.3, 57.8, 44.9, 38.7, 38.0, 27.4, 26.6, 15.3, 14.9, 14.7, 14.0, 13.9

Example 2

Preparation of N-(2-[N',N'-diethylamino]-5-[N"-(4-fluorophenylsulfonyl)-N"-ethylamino]pyrimidin-4-yl)-4'-(pyrrolidin-1-ylcarbonyloxy)-L-phenylalanine Steps 1, 2, 3, 4, 6 and 7 were performed as for Example 1. Step 5 was performed using 4-fluorobenzenesulfonyl chloride in place of 4-chlorobenzenesulfonyl chloride.

$^1$H NMR (CD$_3$OD) δ 8.17 (bs, 1H), 7.90–7.87 (m, 2H), 7.40–7.34 (m, 2H), 7.20–7.16 (m, 1H), 7.08–7.00 (m, 3H), 5.52–5.51 (m, 1H), 4.96–4.93 (m, 2H), 5.78–5.70 (m, 1H), 3.85–3.75 (m, 1H), 3.59–3.53 (m, 4H), 4.47–4.43 (m, 2H), 3.44–3.24 (m, 2H), 2.02–1.94 (m, 3H), 1.24–1.16 (m, 6H), 1.10–1.05 (t, 1.5H), 0.99–0.94 (t, 1.5H) $^{13}$C NMR (CD$_3$OD) δ 133.0, 132.9, 132.5, 132.2, 123.7, 123.6, 118.6, 57.1, 44.3, 38.3, 27.3, 26.6, 14.7, 14.1 MS m/z 629.5 (MH+)

Example 3

Preparation of N-(2-[N',N'-diethylamino]-5-[N"-(4-fluorophenylsulfonyl)-N"-methylamino]pyrimidin-4-yl)-4'-(pyrrolidin-1-ylcarbonyloxy)-L-phenylalanine Steps 1, 2, 3, 4, 5 and 7 were performed as for Example 2. Step 6 was performed using dimethyl sulfate in place of ethyl iodide.

$^1$H NMR (CD$_3$OD) δ 8.16 (bs, 1H), 7.89–7.88 (m, 1H), 7.39–7.35 (m, 3H), 7.20–7.13 (m, 1H), 7.05–7.00 (m, 2H), 4.85–4.84 (m, 1H), 4.14–4.12 (m, 1H), 3.59–3.54 (m, 5H), 3.45–3.44 (m, 2H), 3.45–3.33 (m, 3H), 3.13–3.12 (m, 1H), 3.02–3.01 (m, 1H), 2.04–1.95 (m, 4H), 1.29–1.18 (m, 6H) $^{13}$C NMR (CD$_3$OD) δ 176.5, 169.8, 166.9, 166.4, 156.2, 152.7, 151.8, 150.4, 136.8, 133.3, 133.2, 132.5, 123.7, 118.8, 118.5, 57.8, 57.1, 48.3, 44.5, 41.0, 38.8, 27.5, 26.7, 14.1 MS m/z 615.2 (MH+)

Example 4

Preparation of N-(2-[N',N'-diethylamino]-5-[N"-(4-chlorophenylsulfonyl)-N"-methylamino]pyrimidin-4-yl)-4'-(pyrrolidin-1-ylcarbonyloxy)-L-phenylalanine Steps 1, 2, 3, 4, 5 and 7 were performed as for Example 1. Step 6 was performed using dimethyl sulfate in place of ethyl iodide.

$^1$H NMR (CD$_3$OD) δ 8.20 (bs, 1H), 7.83–7.80 (m, 2H), 7.67–7.64 (m, 2H), 7.37–7.34 (m, 1H), 7.21–7.18 (m, 1H), 7.10–7.03 (m, 2H), 4.88–4.87 (m, 1H), 4.13–4.10 (m, 1H), 3.55–3.45 (m, 6H), 3.42–3.40 (m, 2H), 3.24–3.23 (m, 2H), 3.11–3.10 (m, 1H), 3.02–3.01 (m, 1H), 2.04–2.03 (m, 1H), 1.98–1.90 (m, 3H), 1.28–1.18 (m, 6H) $^{13}$C NMR(CD$_3$OD) δ 176.0, 166.4, 161.8, 155.9, 155.4, 152.6, 146.5, 142.2, 137.6, 137.4, 136.4, 132.5, 131.9, 123.7, 114.6, 62.4, 58.1, 57.7, 45.0, 40.8, 38.6, 38.3, 27.4, 26.6, 15.3, 13.9

Example 5

Preparation of N-(2-[N',N'-diethylamino]-5-[N"-(4-fluorophenylsulfonyl)-N"-methylamino]pyrimidin-4-yl)-4'-(piperidin-1-ylcarbonyloxy)-L-phenylalanine Steps 1, 2, 4, 5, 6 and 7 were performed as for Example 3. Step 3 was performed using 1-piperidinecarbonyl chloride in place of 1-pyrrolidinecarbonyl chloride.

$^1$H NMR (CD$_3$OD) δ 8.16 (bs, 1H), 7.90–7.88 (m, 2H), 7.40–7.35 (m, 2H), 7.21–7.20 (m, 1H), 7.14–7.13 (m, 1H), 7.02–7.01 (m, 2H), 5.51 (bs, 1H), 4.83–4.77 (m, 1H), 3.64–3.53 (m, 6H), 3.34–3.33 (m, 2H), 3.20–3.17 (m, 1H), 3.12–3.11 (m, 2H), 3.02–3.01 (m, 1H), 1.68–1.65 (m, 6H), 1.19–1.17 (m, 6H) $^{13}$C NMR (CD$_3$OD) δ 185.0, 169.7, 166.3, 152.7, 136.6, 135.0, 133.2, 133.0, 132.5, 131.8, 126.3, 123.6, 121.7, 118.6, 118.3, 57.6, 54.5, 46.9, 44.3, 39.6, 38.7, 27.6, 25.9, 14.0

Example 6

Preparation of N-(2-[N',N'-diethylamino]-5-[N"-(4-fluorophenylsulfonyl)-N"-ethylamino]pyrimidin-4-yl)-4'-(piperidin-1-ylcarbonyloxy)-L-phenylalanine Steps 1, 2, 4, 5, 6 and 7 were performed as for Example 2. Step 3 was performed using 1-piperidinecarbonyl chloride in place of 1-pyrrolidinecarbonyl chloride.

$^1$H NMR (CD$_3$OD) δ 8.17 (bs, 1H), 7.91–7.85 (m, 2H), 7.39–7.31 (m, 3H), 7.20–7.16 (m, 1H), 7.05–6.97 (m, 2H), 4.88–4.69 (m, 2H), 4.71–4.69 (m, 1H), 3.80–3.75 (m, 1H), 3.62–3.39 (m, 6H), 3.34–3.32 (m, 2H), 3.30–3.16 (m, 3H), 1.68–1.65 (m, 4H), 1.23–1.17 (m, 6H), 1.10–1.05 (t, 1.5H), 0.99–0.94 (t, 1.5H) $^{13}$C NMR (CD$_3$OD) δ 199.9, 187.6, 183.1, 176.2, 169.7, 166.3, 163.0, 162.7, 153.9, 152.9, 136.5, 133.1, 133.0, 132.7, 132.4, 123.8, 118.8, 118.4, 111.1, 110.6, 102.8, 79.4, 57.3, 55.4, 44.4, 38.9, 38.4, 27.7, 26.1, 15.1, 14.8, 14.3, 14.2

Example 7

Preparation of N-(2-[N',N'-diethylamino]-5-[N"-(4-fluorophenylsulfonyl)-N"-ethylamino]pyrimidin-4-yl)-4'-(azetidin-1-ylcarbonyloxy)-L-phenylalanine Steps 1, 2, 4, 5, 6 and 7 were performed as for Example 2. Step 3 was performed according to the following procedure.

$^1$H NMR (CD$_3$OD) δ 7.92–7.86 (m, 2H), 7.41–7.32 (m, 3H), 7.22 (d, 1H), 7.04–6.91 (m, 3H), 4.29–3.98 (m, 4H), 3.88–3.72 (m, 1H), 3.69–3.37 (m, 4H), 2.40–2.24 (m, 2H), 1.28–1.11 (m, 6H), 1.10–1.00 (t, 1.5H), 1.01–0.89 (t, 1.5H) $^{13}$C NMR (CD$_3$OD) δ 174.2, 169.7, 166.4, 163.2, 162.8, 157.0, 153.3, 153.2, 152.4, 144.3, 143.8, 136.1, 135.6, 135.5, 133.2, 133.1, 132.5, 132.2, 123.7, 118.9, 118.6, 112.9, 112.6, 57.5, 38.1, 37.7, 17.4, 14.7, 14.5, 13.8, 13.7 MS m/z 615 (MH$^+$)

Alternative Preparation of N-(2-[N',N'-diethylamino]-5-nitropyrimidin-4-yl)-4'-(azetidin-1-ylcarbonyloxy)-L-phenylalanine tert-butyl ester. To a −15° C. stirred solution of compound 3 (24.9 g, 0.0578 mol) and 4-nitrophenyl chloroformate (11.7 g, 0.0578 mmol) in CH$_2$Cl$_2$ (300 mL) was added triethylamine (24.2 mL, 0.173 mol), at a rate such that the temperature of the reaction mixture did not exceed −10° C. After stirring for 20 min, azetidine (3.30 g, 0.0578 mmol) was added dropwise, and the reaction mixtures was warmed to room temperature and stirred overnight. The reaction mixture was diluted with EtOAc (100 mL) and hexanes (100 mL), and then was extracted repeatedly with 10% aqueous K$_2$CO$_3$, until no yellow color (4-nitrophenol) was seen in the aqueous phase. The organic layer was washed with brine (75 mL), dried with MgSO$_4$, filtered, and evaporated to yield 28.5 g (96%) of N-(2-[N',N'-diethylamino]-5-nitropyrimidin-4-yl)-4'-(azetidin-1-ylcarbonyloxy)-L-phenylalanine tert-butyl ester as a yellow solid, which was used without purification. R$_f$=0.17 (2:5 EtOAc/hexanes on silica gel).

Example 8

Preparation of N-(2-[N',N'-diethylamino]-5-[N"-(4-fluorophenylsulfonyl)-N"-methylamino]pyrimidin-4-yl)-4'-(azetidin-1-ylcarbonyloxy)-L-phenylalanine Steps 1, 2, 3, 4, 5 and 7 were performed as for Example 7. Step 6 was performed using dimethyl sulfate in place of ethyl iodide.

$^1$H NMR (CD$_3$OD) δ 7.95–7.76 (m, 2H), 7.44–7.11 (m, 4H), 7.01–6.83 (m, 3H), 4.30–3.93 (m, 4H), 3.66–3.41 (m, 4H), 3.14–2.92 (m, 3H), 2.42–2.21 (m, 2H), 1.32–1.01 (m, 6H) $^{13}$C NMR (CD$_3$OD) δ 152.3, 136.3, 133.4, 133.2, 132.4, 123.6, 118.8, 118.5, 38.2, 17.4, 13.8 MS m/z 601 (MH$^+$)

Example 9

Preparation of N-(2-[N',N'-diethylamino]-5-[N"-(4-chlorophenylsulfonyl)-N"-methylaminolpyrimidin-4-yl)-4'-(azetidin-1-ylcarbonyloxy)-L-phenylalanine Steps 1, 2, 3, 4, 6 and 7 were performed as for Example 8. Step 5 was performed using 4-chlorobenzenesulfonyl chloride in place of 4-fluorobenzensulfonyl chloride.

$^1$H NMR (CD$_3$OD) δ 7.83 (d, 2H), 7.67 (d, 2H), 7.36–7.18 (m, 2H), 7.06–6.86 (m, 3H), 4.29–3.97 (m, 4H), 3.66–3.34 (m, 5H), 3.15–2.95 (m, 4H), 2.41–2.22 (m, 2H) 1.26–1.06 (m, 6H) $^{13}$C NMR (CD$_3$OD) δ 157.2, 153.0, 152.5, 142.9, 142.5, 136.4, 132.5, 132.1, 132.0, 123.8, 57.9, 52.2, 40.7, 38.0, 17.4, 13.6 MS m/z 617 (MH$^+$)

Example 10

Preparation of N-(2-[N',N'-diethylamino]-5-[N"-(4-chlorophenylsulfonyl]-N"-ethylamino]pyrimidin-4-yl)-4'-(azetidin-1-ylcarbonyloxy)-L-phenylalanine Steps 1, 2, 3, 4, 6 and 7 were performed as for Example 7. Step 5 was performed using 4-chlorobenzenesulfonyl chloride in place of 4-fluorobenzensulfonyl chloride.

$^1$H NMR (CD$_3$OD) δ 7.86–7.76 (m, 2H), 7.70–7.60 (m, 2H), 7.32 (bd, 1H), 7.21 (bd, 1H), 7.03–6.97 (m, 2H), 6.90 (bs, 1H), 4.29–4.00 (m, 4H), 3.89–3.72 (m, 1H), 3.70–3.36 (m, 5H), 3.28–3.10 (m, 2H), 2.42–2.24 (m, 2H), 1.28–1.13 (m, 6H), 1.11–1.02 (t, 1.5H), 1.01–0.90 (t, 1.5H) MS m/z 631 (MH$^+$)

Example 11

Preparation of N-(2-[N',N'-diethylamino]-5-[N"-(2,4-difluorophenylsulfonyl)-N"-methylamino]pyrimidin-4-yl)-4'-(pyrrolidin-1-ylcarbonyloxy)-L-phenylalanine Steps 1, 2, 3, 4, 6 and 7 were performed as for Example 3. Step 5 was performed using 2,4-difluorobenzenesulfonyl chloride in place of 4-fluorobenzensulfonyl chloride.

$^1$H NMR (CDCl$_3$) δ 1.16 (bs, 6H), 1.93 (bs, 4H), 2.50–3.75 (m, 13H), 4.83 (bs, 1H), 6.60–7.40 (m, 7H), 7.60 (bs, 1H), 7.77 (m, 1H), 9.41 (bs, 1H)

Example 12

Preparation of N-(2-[N',N'-diethylamino]-5-[N"-(2,4-difluorophenylsulfonyl)-N"-ethylamino]pyrimidin-4-yl)-4'-(pyrrolidin-1-ylcarbonyloxy)-L-phenylalanine Steps 1, 2, 3, 4, 6 and 7 were performed as for Example 2. Step 5 was performed using 2,4-difluorobenzenesulfonyl chloride in place of 4-fluorobenzensulfonyl chloride.

$^1$H NMR (CDCl$_3$) δ 0.91 (t, J=6.9, 1.8H), 1.12 (m, 7.2H), 1.92 (bs, 4H), 2.50–4.00 (m, 13H), 4.78 (m, 0.6H), 4.88 (m, 0.4H), 6.55 (d, J=6.9, 0.4H), 6.77 (d, J=6.3, 0.6H), 6.80–7.38 (m, 6H), 7.51 (s, 0.4H), 7.58 (s, 0.6H), 7.74 (m, 1H), 9.33 (m, 1H)

Example 13

Preparation of N-(2-[N',N'-diethylamino]-5-[N"-(2,4-difluorophenylsulfonyl)-N"-methylamino]pyrimidin-4-yl)-4'-(azetidin-1-ylcarbonyloxy)-L-phenylalanine Steps 1, 2, 4, 5, 6 and 7 were performed as for Example 11. Step 3 was performed as for Example 7.

$^1$H NMR (CDCl$_3$) δ 1.14 (t, J=6.6, 6H), 2.32 (m, 2H), 2.50–3.80 (m, 9H), 4.13 (m, 4H), 4.62 (m, 0.6H), 4.81 (m, 0.4H), 5.81 (bd, 0.6H), 5.90 (bd, 0.4H), 6.90–7.40 (m, 7H), 7.77 (m, 1H) MS m/z 619.2 (MH$^+$)

Example 14

Preparation of N-(2-[N',N'-diethylamino]-5-[N"-(2,4-difluorophenylsulfonyl)-N"-ethylamino]pyrimidin-4-yl)-4'-(azetidin-1-ylcarbonyloxy)-L-phenylalanine Steps 1, 2, 4, 5, 6 and 7 were performed as for Example 12. Step 3 was performed as for Example 7.

$^1$H NMR (CDCl$_3$) δ 0.89 (t, J=6.7, 1.8H), 1.16 (m, 7.2H), 2.28 (m, 2H), 3.00–4.00 (m, 8H), 4.09 (bs, 4H), 4.79 (m, 0.6H), 4.88 (m, 0.4H), 6.80–7.30 (m, 7H), 7.57 (s, 0.4H), 7.62 (s, 0.6H), 7.75 (m, 1H), 11.9 (bs, 1H) MS m/z 633.2 (MH$^+$)

Example 15

Preparation of N-(2-[N',N'-diethylamino]-5-[N"-(4-fluorophenylsulfonyl)-N"-propargylamino]pyrimidin-4-yl)-4'-(pyrrolidin-1-ylcarbonyloxy)-L-phenylalanine Steps 1, 2, 3, 4, 5 and 7 were performed as for Example 2. Step 6 was performed using propargyl bromide in place of ethyl iodide.

$^1$H NMR (CDCl$_3$) δ 1.18 (m, 6H), 1.93 (bs, 4H), 2.37 (s, 1H), 3.00–3.70 (m, 10H), 3.80 (d,J=21.3, 0.6H), 3.98 (d,J=18.3, 0.4H), 4.51 (m, 1H), 4.88 (m, 1H), 6.75–7.35 (m, 7H), 7.58 (s, 0.6H), 7.63 (s, 0.4H), 7.86 (m, 2H), 9.71 (bs, 1H)

Example 16

Preparation of N-(2-[N',N'-diethylamino]-5-[N'''-(2,4-difluorophenylsulfonyl)-N'''-propargylamino]pyrimidin-4-yl)-4'-(pyrrolidin-1-ylcarbonyloxy)-L-phenylalanine Steps 1, 2, 3, 4, 5 and 7 were performed as for Example 11. Step 6 was performed using propargyl bromide in place of dimethyl sulfate.

$^1$H NMR (CDCl$_3$) δ 1.17 (m, 6H), 1.94 (m, 4H), 2.40 (m, 1H), 3.00–3.75 (m, 10H), 3.99 (d, J=18.0, 0.6H), 4.18 (d, J=18.0, 0.4H), 4.50 (m, 1H), 4.90 (m, 1H), 6.75–7.35 (m, 7H), 7.81 (m, 2H), 10.0 (bs, 1H)

Example 17

Preparation of N-(2-[N',N'-diethylamino]-5-[N'''-(2,4-difluorophenylsulfonyl)-N'''-propargylamino]pyrimidin-4-yl)-4'-(azetidin-1-ylcarbonyloxy)-L-phenylalanine Steps 1, 2, 4, 5, 6 and 7 were performed as for Example 16. Step 3 was performed as for Example 7.

$^1$H NMR (CDCl$_3$) δ 1.18 (m, 6H), 2.34 (m, 3H), 3.00–3.75 (m, 6H), 3.80–4.25 (m, 5H), 4.47 (m, 1H), 4.89 (m, 1H), 6.75–7.35 (m, 7H), 7.79 (m, 2H), 10.3 (bs, 1H) MS m/z 643.2 (MH$^+$)

Example 18

Preparation of N-(2-[N',N'-diethylamino]-5-[N'''-(4-fluorophenylsulfonyl)-N'''-propargylamino]pyrimidin-4-yl)-4'-(azetidin-1-ylcarbonyloxy)-L-phenylalanine Steps 1, 2, 3, 4, 5 and 7 were performed as for Example 7. Step 6 was performed using propargyl bromide in place of ethyl iodide.

$^1$H NMR (CDCl$_3$) δ 1.25 (m, 6H), 2.28 (m, 3H), 3.00–3.75 (m, 6H), 3.80–4.25 (m, 5H), 4.47 (m, 1H), 4.89 (m, 1H), 6.75–7.35 (m, 7H), 7.57 (s, 0.6H), 7.62 (s, 0.4H), 7.79 (m, 2H), 10.6 (bs, 1H) MS m/z 625.2 (MH$^+$)

Example 19

Preparation of N-(2-[N',N'-diethylamino]-5-[N'''-(4-chlorophenylsulfonyl)-N'''-propargylamino]pyrimidin-4-yl)-4'-(pyrrolidin-1-ylcarbonyloxy)-L-phenylalanine Steps 1, 2, 3, 4, 5 and 7 were performed as for Example 1. Step 6 was performed using propargyl bromide in place of ethyl iodide.

$^1$H NMR (CD$_3$OD) δ 8.13 (s, 1H), 7.86–7.82 (m, 2H), 7.62–7.58 (m, 2H), 7.32–7.28 (m, 2H), 7.19–7.17 (m, 1H), 7.04–6.98 (m, 2H), 4.83–4.5 (m, 2H), 4.12–3.82 (m, 1H), 3.63–3.37 (m, 8H), 3.27–3.08 (m, 2H), 2.72 (bs, 1H), 2.04–1.86 (m, 4H), 1.24–1.07 (m, 6H) $^{13}$C NMR (CD$_3$OD) δ 177.2, 176.5, 162.7, 156.7, 155.7, 154.5, 153.2, 142.6, 140.3, 137.4, 137.3, 133.1, 132.9, 132.8, 132.7, 132.2, 132.1, 124.3, 111.3, 80.5, 80.3, 77.7, 58.2, 57.7, 44.9, 43.4, 28.1, 27.3, 14.8, 14.7 MS m/z 655 (MH$^+$)

The following methods may be used to test compounds of this invention.

Example A

α$^4$β$^1$ Integrin Adhesion Assay: Jurkat™ Cell Adhesion to Human Plasma Fibronectin Procedure:

96 well plates (Costar 3590 EIA plates) were coated with human fibronectin (Gibco/BRL, cat #33016–023) at a concentration of 10 µg/mL overnight at 4° C. The plates were then blocked with a solution of bovine serum albumin (BSA; 0.3%) in saline. Jurkat™ cells (maintained in log phase growth) were labeled with Calcein AM according to the manufacturer's instructions, and suspended at a concentration of 2×10$^6$ cells/mL in Hepes/Saline/BSA. The cells were then exposed to test and control compounds for 30 minutes at room temperature before transfer to individual wells of the fibronectin coated plate. Adhesion was allowed to occur for 35 minutes at 37° C. The wells were then washed by gentle aspiration and pipetting with fresh saline. Fluorescence associated with the remaining adherent cells was quantified using a fluorescence plate reader at EX 485/EM 530.

Cell cultures were prepared by first splitting the stationary phase Jurkat™ cells at 1:10 on day one, and 1:2 on day two to perform assay on day 3. The cells split 1:10 on day one were split 1:4 on day 3 for a day 4 assay.

The assay plates were prepared by first making a working solution of Gibco/BRL Human Fibronectin (cat #33016-023) in PBS++, at 10 µg/mL. A Costar 3590 EIA plate was then coated with 50 µL/well for 2 hours at room temperature (thought it can also be left overnight at 4° C.). Finally the plate was asperated and blocked with Hepes/Saline Buffer, 100 µL/well, for 1 hour at RT followed by washing 3× with 150 µL of PBS++.

Compound dilutions were accomplished by preparing 1:3 serial dilutions of compounds as follows. For each plate (4 compounds/plate) 600 µL were added to 4 Bio-Rad Titertubes in a Titertube rack. Enough compound was added to each appropriate tube to give a 2× concentration using methods well known in the art. Using Falcon Flexiplates, 100 µL of Hepes/Saline buffer or human serum were added to rows B through G. A multi-channel pipetter set to 180 µL was used to with four tips spaced evenly the pipetter. Each set of four tubes was mixed 5 times and 180 µL of 2× compound was transferred to the first column of each compound dilution in Row B, leaving Row A empty. 180 µL were added to the other wells in Row A. Serial dilutions were performed down the plate by transferring 50 µL to the next dilution and mixing 5 times, changing tips each time after mixing. Dilutions were stopped at Row F. Row G had no compound present.

A 20 µg/mL solution in Hepes/Saline buffer or human serum, of 21/6 antibody was the positive control and was set aside in a reagent trough to add to cell suspension plate.

The cell staining was accomplished by first harvesting the log-phase Jurkat™ cells by centrifugation in 50 mL tubes (1100 rpm for 5 minutes). The cells were resuspended in 50 mL PBS++, spun, and resuspend in 20 mL PBS++. The cells were stained by adding 20 µL of Calcein AM for 30 minutes RT. The volume was brought to 50 mL with Hepes/Saline buffer and the cells were counted, spun, and resuspend to 2×10$^6$ cells/mL in Hepes/Saline buffer or human serum.

The compounds were incubated using the following procedure. In a new flexiplate, 65 µL of stained cells were added to Rows B through H. Then 65 µL of 2× compounds were added to the appropriate rows following the plate setup and mixed three times. 65 μL of 2×-21/6 antibody were added to Row H and mixed 3×. Finally the plate was incubated at room temperature for 30 minutes.

Fibronectin adhesion was measured using a fluorescent plate reader at EX 485/EM 530 after the following work up procedure. After incubation, the cells were mixed three times and 100 μL were transferred to the Fibronectin coated plates and incubated at 37° C. for about 35 minutes. Each plate was washed, row by row, by gently pipetting 100 μL of RT. PBS++ down the sides of the wells and turning the plate 90 degrees to aspirate. This procedure was repeated for a total of 3 washes. Each well was filled with 100 μL after washing by pipetting down the side of the well.

An $IC_{50}$ value was calculated for each compound, both in the presence of the human serum and in the absence of human serum. $IC_{50}$ is concentration at which the growth or activity is inhibited by 50%. The data is presented in the following tables.

| Cell Adhesion to Human Plasma Fibronectin (Without the human serum) | |
|---|---|
| Example No. | $IC_{50}$ (ug/mL) |
| 1. | 0.011 |
| 2. | 0.001 |
| 3. | 0.004 |
| 4. | 0.012 |
| 5. | 0.00377 |
| 6. | 0.003 |
| 7. | 0.001 |
| 8. | 0.001 |
| 9. | 0.002 |
| 10. | 0.00256 |
| 11. | 0.005293 |
| 12. | 0.005632 |
| 13. | 0.001515 |
| 14. | 0.002146 |
| 15. | 0.063 |
| 16. | 0.009 |
| 17. | 0.00337 |
| 18. | 0.003663 |
| 19. | 0.004538 |

| Cell Adhesion to Human Plasma Fibronectin (Containing human serum) | |
|---|---|
| Example No. | $IC_{50}$ (ug/mL) |
| 1. | 0.264 |
| 2. | 0.38 |
| 3. | 1.062 |
| 4. | 1.437 |
| 5. | 0.987 |
| 6. | 0.451 |
| 7. | 0.053 |
| 8. | 0.135 |
| 9. | 0.128 |
| 10. | 0.052332 |
| 11. | 0.305436 |
| 12. | 0.147085 |
| 13. | 0.055391 |
| 14. | 0.03259 |
| 15. | 1.102 |
| 16. | 0.371 |
| 17. | 0.080426 |
| 18. | 0.3 |
| 19. | 4.114982 |

Example B

In Vitro Saturation Assay for Determining Binding of Candidate Compounds to $\alpha_4\beta_1$ The following describes an in vitro assay to determine the plasma levels needed for a compound to be active in the Experimental Autoimmune Encephalomyelitis ("EAE") model, described in the next example, or in other in vivo models.

Log-growth Jurkat cells are washed and resuspended in normal animal plasma containing 20 μg/mL of the 15/7 antibody (Yednock, et al., *J. Biol. Chem.*, (1995) 270(48): 28740).

The Jurkat cells are diluted two-fold into either normal plasma samples containing known candidate compound amounts in various concentrations ranging from 66 μM to 0.01 μM, using a standard 12 point serial dilution for a standard curve, or into plasma samples obtained from the peripheral blood of candidate compound-treated animals.

Cells are then incubated for 30 minutes at room temperature, washed twice with phosphate-buffered saline ("PBS") containing 2% fetal bovine serum and 1 mM each of calcium chloride and magnesium chloride (assay medium) to remove unbound 15/7 antibody.

The cells are then exposed to phycoerythrin-conjugated goat F(ab')$_2$ anti-mouse IgG Fc (Immunotech, Westbrook, Me.), which has been adsorbed for any non-specific cross-reactivity by co-incubation with 5% serum from the animal species being studied, at 1:200 and incubated in the dark at 4° C. for 30 minutes.

Cells are washed twice with assay medium and resuspended in the same. They are then analyzed with a standard fluorescence activated cell sorter ("FACS") analysis as described in Yednock et al. J. Biol. Chem., 1995, 270:28740.

The data is then graphed as fluorescence versus dose, e.g., in a normal dose-response fashion. The dose levels that result in the upper plateau of the curve represent the levels needed to obtain efficacy in an in vivo model.

Example C

Cassette Dosing and Serum Analysis for Determination of Bioavailability

The oral bioavailability was screened by dosing rats with a cassette, i.e. mixture of 6 compounds per dosing solution. The cassette included 5 test articles and a standard compound, for a total dose of 10 mg/kg. Each compound/test article was converted to the sodium salt with equimolar 1 N NaOH and dissolved in water at 2 mg/mL. The cassette was prepared by mixing equal volumes of each of the six solutions. The cassette dosing solution was mixed well and then the pH was adjusted to 7.5–9. The dosing solution was prepared the day before the study and stirred overnight at room temperature.

Male Sprague Dawley (SD) rats from Charles River Laboratories, 6–8 weeks old were used in this screen. Rats were quarantined for at least one day and had continuous access to food and water. On the night before the administration of the cassette, the rats were fasted for approximately 16 h.

Four SD rats were assigned in each cassette. A single dose of the dosing solution was administered orally to each rat. The dosing volume (5 mL/kg) and time were recorded and rats were fed 2 h after dosing.

Blood samples were collected via cardiac puncture at the following time points: 4 h, 8 h and 12 h. Immediately prior to blood collection, rats were anesthetized with $CO_2$ gas within 10–20 seconds. After the 12-h samples were collected, the rats were euthanized via $CO_2$ asphyxiation followed by cervical dislocation.

Blood samples were kept in heparinized microtainer tubes under sub-ambient temperature (4° C.) before they were processed. Blood samples were centrifuged (10000 rpm for 5 minutes) and plasma samples were removed and stored in a −20° C. freezer until analyzed for drug levels. Drug levels in the plasma were analyzed using the following protocol for direct plasma precipitation.

The in vivo plasma samples were prepared in a 1.5 mL 96-well plate, by adding, in order, 100 μL of the test plasma, 150 μL of methanol, followed by vortexing for 10–20 seconds. 150 μL of 0.05 ng/μL of an Internal Standard in acetonitrile were added and vortexed for 30 seconds.

The standard curve samples were prepared in a 1.5 mL 96-well plate, by adding, in order, 100 μL of control mouse plasma, followed by 150 μL of methanol and vortexing for 10–20 seconds. 150 μL of 0.05 ng/μL of an Internal Standard in acetonitrile were added and vortexed for 30 seconds. The samples were spiked with 0–200 ng (10 concentrations) of the compound of interest in 50% methanol to obtain a standard curve range of 0.5 ng/mL–2,000 ng/mL. Again, the sample was vortexed for 30 seconds.

The samples were then spun for 20–30 minutes at 3000 rpm in an Eppendorf microfuge before 80–90% of supernatant was transferred into a clean 96-well plate. The organic solvent was then evaporated until the samples were dry (under $N_2$ at 40° C./30–60 min (Zymark Turbovap)).

The residue was then dissolved in 200–600 L mobile phase (50% $CH_3OH$/0.1% TFA). LC/MS/MS was then run using a PE-Sciex API-3000 triple quadurpole mass spectrometer (SN0749707), Perkin-Elmer, Series200auto-sampler, and shimadzu 10A pump. Acquisition was done with PE-Sciex Analyst (v1.1) and data analysis and quantification were accomplished using PE-Sciex Analyst (v1.1). A 5–50 μL sample volume was injected onto a reverse phase ThermoHypersil DASH-18 column (Keystone 2.0×20 mm, 5 μm, PN: 8823025-701) using a mobile phase of 25% $CH_3OH$, 0.1% TFA-100% $CH_3OH$, 0.1% TFA. The run time was about 8 minutes at a flow rate of about 300 μL/minutes.

The Area Under the Curve (AUC) was calculated using the linear trapezoidal rule from t=0 to the last sampling time $t_x$ (see Handbook of Basic Pharmacokinetics, Wolfgang A. Ritschel and Gregory L. Kearns, $5^{th}$ ed, 1999).

$$AUC^{0 \to tx} = S((C_n + C_{n+1})/2) \cdot (t_{n+1} - t_n)[(\mu g/mL)h]$$

In the case of the cassette dosing paradigm, samples at 4, 8 and 12 h post extravascular dosing, the AUC was calculated from t=0 to t=12 h. The $AUC^{0 \to 12\ h}$ values were calculated for each individual animal and the average $AUC^{0 \to 12\ h}$ are reported in the table below.

| Example No. | AUC |
|---|---|
| 1. | 14.798 |
| 2. | 15.971 |
| 3. | 22.271 |
| 4. | 13.829 |
| 5. | 2.1654 |
| 6. | 0.5125 |
| 7. | 0.8979 |
| 8. | 2.4082 |

-continued

| Example No. | AUC |
|---|---|
| 9. | 2.0774 |
| 10. | 2.1113 |
| 11. | 14.818 |
| 12. | 4.7816 |
| 13. | 1.283 |
| 14. | 0.3566 |
| 15. | 90.317 |
| 16. | 23.808 |
| 17. | 0.8628 |
| 18. | 4.7528 |

Example D

Asthma Models

Inflammatory conditions mediated by $\alpha_4\beta_1$ integrin include, for example, eosinophil influx, airway hyper-responsiveness and occlusion that occurs with chronic asthma. The following describes animal models of asthma that were used to study the in vivo effects of the compounds of this invention for use in treating asthma.

Rat Asthma Model

This model follows the procedures described by Chapman et al, Am J. Resp. Crit. Care Med, 153 4, A219 (1996) and Chapman et al, Am. J. Resp. Crit Care Med 155:4, A881 (1997), both of which are incorporated by reference in their entirety. Ovalbumin (OA; 10 mg/mL) were mixed with aluminum hydroxide (10 mg/mL) and injected (i.p.) in Brown Norway rats on day 0. Injections of OA, together with adjuvant, were repeated on days 7 and 14. On day 21, sensitized animals were restrained in plastic tubes and exposed (60 minutes) to an aerosol of OA (10 mg/kg) in a nose-only exposure system. Animals will be sacraficed 72 hours later with pentobarbital (250 mg/kg, i.p.). The lungs were lavaged via a tracheal cannula using 3 aliquots (4 mL) of Hank's solution (HBSS×10, 100 mL; EDTA 100 mM, 100 mL; HEPES 1 M, 25 mL; made up to 1 L with $H_2O$); recovered cells were pooled and the total volume of recovered fluid adjusted to 12 mL by addition of Hank's solution. Total cells were counted (Sysmex microcell counter F-500, TOA Medical Electronics Otd., Japan) and smears were made by diluting recovered fluid (to approximately $10^6$ cells/mL) and pipetting an aliquot (100 μL) into a centrifuge (Cytospin, Shandon, U.K.). Smears were air dried, fixed using a solution of fast green in methanol (2 mg/mL) for 5 seconds and stained with eosin G (5 seconds) and thiazine (5 seconds) (Diff-Quick, Browne Ltd. U.K.) in order to differentiate eosinophils, neutrophils, macrophages and lymphocytes. A total of 500 cells per smear were counted by light microscopy under oil immersion (×100). Compounds of this invention were formulated into a 0.5% carboxymethylcellulose and 2% Tween80 suspension and administered orally to rats which had been sensitized to the allergen, ovalbumin. Compounds which inhibited allergen-induced leucocyte accumulation in the airways of actively sensitized Brown Norway rats were considered to be active in this model.

Mouse Asthma Model

Compounds were also evaluated in a mouse model of acute pulmonary inflammation following the procedures described by, Kung et al., Am J. Respir. Cell Mol. Biol. 13:360–365, (1995) and Schneider et al., (1999). Am J. Respir. Cell Mol. Biol. 20:448–457, (1999), which are each incorporated by reference in their entirety. Female Black/6 mice (8–12 weeks of age) were sensitized on day 1 by an intraperitoneal injection (i.p.) of 0.2 mL ova/alum mixture containing 20 μg of ova (Grade 4, Sigma) and 2 mg inject Alum (Pierce). A booster injection was administered on day 14. Mice are challenged on days 28 and 29 with aerosolized 1% ova (in 0.9% saline) for 20 minutes. Mice are euthanized and bronchaveolar lavage samples (3 mL) are collected on day 30, 48 hours post first challenge. Eosinophils were quantified by a FACs/FITC staining method. Compounds of this invention were formulated into a 0.5% carboxymethylcellulose and 2% Tween80 suspension and administered orally to mice which had been sensitized to the allergen, ovalbumin. Compounds which inhibited allergen-induced leucocyte accumulation in the airways of actively sensitized C57BL/6 mice were considered to be active in this model.

Sheep Asthma Model

This model follows the procedures described by Abraham et al, J. Clin, Invest, 93:776–787 (1994) and Abraham et al, Am J. Respir Crit Care Med 156:696–703 (1997), both of which are incorporated by reference in their entirety. Compounds of this invention have been evaluated by intravenous (saline aqueous solution), oral (2% Tween80, 0.5% carboxymethylcellulose), and aerosol administration to sheep which are hypersensitive to *Ascaris suum* antigen. Compounds which decrease the early antigen-induced bronchial response and/or block the late-phase airway response, e.g. have a protective effect against antigen-induced late responses and airway hyper-responsiveness ("AHR"), are considered to be active in this model.

Allergic sheep which are shown to develop both early and late bronchial responses to inhaled *Ascaris suum* antigen were used to study the airway effects of the candidate compounds. Following topical anesthesia of the nasal passages with 2% lidocaine, a balloon catheter was advanced through one nostril into the lower esophagus. The animals were then incubated with a cuffed endotracheal tube through the other nostril with a flexible fiberoptic bronchoscope as a guide.

Pleural pressure was estimated according to Abraham (1994). Aerosols (see formulation below) were generated using a disposable medical nebulizer that provided an aerosol with a mass median aerodynamic diameter of 3.2 μm as determined with an Andersen cascade impactor. The nebulizer was connected to a dosimeter system consisting of a solenoid valve and a source of compressed air (20 psi). The output of the nebulizer was directed into a plastic T-piece, one end of which was connected to the inspiratory port of a piston respirator. The solenoid valve was activated for 1 second at the beginning of the inspiratory cycle of the respirator. Aerosols were delivered at $V_T$ of 500 mL and a rate of 20 breaths/minute. A 0.5% sodium bicarbonate solution only was used as a control.

To assess bronchial responsiveness, cumulative concentration-response curves to carbachol was generated according to Abraham (1994). Bronchial biopsies were taken prior to and following the initiation of treatment and 24 hours after antigen challenge. Bronchial biopsies were preformed according to Abraham (1994).

An in vitro adhesion study of alveolar macrophages were also performed according to Abraham (1994), and a percentage of adherent cells calculated.

Aerosol Formulation

A solution of the candidate compound in 0.5% sodium bicarbonate/saline (w/v) at a concentration of 30.0 mg/mL is prepared using the following procedure:

| A. Preparation of 0.5% Sodium Bicarbonate/Saline Stock Solution: 100.0 mL | | |
|---|---|---|
| Ingredient | Gram/100.0 mL | Final Concentration |
| Sodium Bicarbonate | 0.5 g | 0.5% |
| Saline | q.s. ad 100.0 mL | q.s. ad 100% |

Procedure:
1. Add 0.5 g sodium bicarbonate into a 100 mL volumetric flask.
2. Add approximately 90.0 mL saline and sonicate until dissolved.
3. Q.S. to 100.0 mL with saline and mix thoroughly.

| B. Preparation of 30.0 mg/mL Candidate Compound: 10.0 mL | | |
|---|---|---|
| Ingredient | Gram/10.0 mL | Final Concentration |
| Candidate Compound | 0.300 g | 30.0 mg/mL |
| 0.5% Sodium Bicarbonate/Saline Stock Solution | q.s. ad 10.0 mL | q.s ad 100% |

Procedure:
1. Add 0.300 g of the candidate compound into a 10.0 mL volumetric flask.
2. Add approximately 9.7 mL of 0.5% sodium bicarbonate/saline stock solution.
3. Sonicate until the candidate compound is completely dissolved.
4. Q.S. to 10.0 mL with 0.5% sodium bicarbonate/saline stock solution and mix thoroughly.

Example E

10-Day Toxicity Study on C57B6 Mice

A 10-day study was conducted to evaluate the toxicity of compounds of the present invention to female C57B6 mice. The compound was administered by gavage at five dose levels, 0 (vehicle control), 10, 30, 100, 300 and 1000 mg/kg (mpk), with five mice in each dose level. The dose volume for all levels was 10 mL/kg. Dose solutions or suspensions were prepared in 2% Tween 80 in 0.5% carboxymethyl cellulose (CMC) and new dose solutions or suspensions were prepared every two–three days. In-life observations included body weights (study day 1, 2, 3, 5, 7, 8 and 11), daily cageside clinical observations (1–2/day) and periodic (study day-1, 2 and 9) functional observation battery.

At termination, blood samples were collected by cardiac puncture for clinical pathology (hematology and clinical chemistry) and drug levels. The EDTA blood samples were analyzed for total white blood cell count, red blood cell count, hemoglobin, hematocrit, erythrocyte indices (MCV, MCH, MCHC), platelets and a WBC five part differential (neutrophil, lymphocytes, monocytes, eosinophils and basophils). Heparinized plasma samples were analyzed for alanine transaminase, aspartate transaminase, alkaline phosphatase, total bilirubin, albumin, protein, calcium, glucose, urea nitrogen, creatinine, cholesterol and triglycerides.

After blood collection, the carcass was necropsied and organs (liver, spleen, kidneys, heart and thymus) were weighed. Tissue samples; brain, salivary glands, thymus, heart, lung, liver, kidney, adrenal spleen, stomach, duodenum, ileum, colon and uterus/ovary, were collected and formalin fixed. Tissues from the vehicle control and 300 and 1000 mpk group animals were processed to H & E stained glass slides and evaluated for histopathological lesions.

Body weight changes, absolute and relative organ weights and clinical pathology results were analyzed for statistical significant differences compared to the vehicle controls by Dunnet's multiple comparison test using Prism software. The functional observation battery results were analyzed for differences using the Dunnet's, Fisher's exact tests and dose trend effects by the Cochran-Mantel-Haenszel correlation test using SAS software.

Using a conventional oral formulation, compounds of this invention would be active in this model.

Example F

Adjuvant-Induced Arthritis in Rats

Adjuvant induced arthritis ("AIA") is an animal model useful in the study of rheumatoid arthritis (RA), which is induced by injecting *M. tuberculosis* in the base of the tail of Lewis rats. Between 10 and 15 days following injection, animals develop a severe, progressive arthritis.

Generally, compounds are tested for their ability to alter hind paw swelling and bone damage resulting from adjuvant-induced edema in rats. To quantitate the inhibition of hind paw swelling resulting from AIA, two phases of inflammation have been defined: (1) the primary and secondary injected hind paw, and (2) the secondary uninjected hind paw, which generally begins developing about eleven days from the induction of inflammation in the injected paw. Reduction of the latter type of inflammation is an indication of immunosuppressive activity. Cf. Chang, Arth. Rheum., 20, 1135–1141 (1977).

Using an animal model of RA, such as AIA, enables one to study the cellular events involved in the early stages of the disease. CD44 expression on macrophages and lymphocytes is up-regulated during the early development of adjuvant arthritis, whereas LFA-1 expression is up-regulated later in the development of the disease. Understanding the interactions between adhesion molecules and endothelium at the earliest stages of adjuvant arthritis could lead to significant advances in the methods used in the treatment of RA.

What is claimed is:

1. A compound of formula (I):

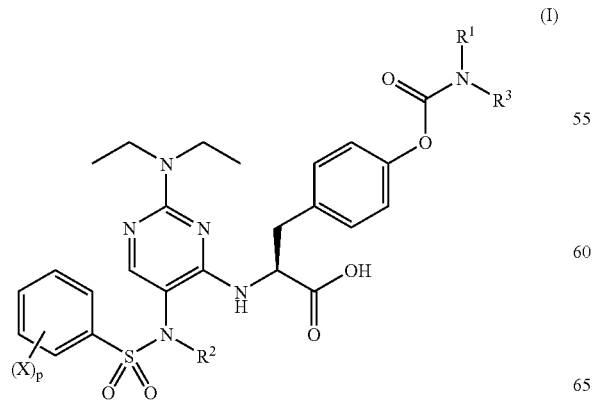

(I)

wherein each X is independently fluoro, chloro or bromo;

p is an integer from 0 to 3;

$R^1$ and $R^3$ together with the nitrogen atom to which they are bound form an azetidinyl, pyrrolidinyl, pyrrolyl, 2,5-dihydropyrrol-1-yl, piperidinyl, or 1,2,3,6-tetrahydro-pyridiny-1-yl group;

$R^2$ is selected from the group consisting of lower alkyl, lower alkenyl, and lower alkylenecycloalkyl;

and pharmaceutically acceptable salts thereof.

2. A compound of Formula II:

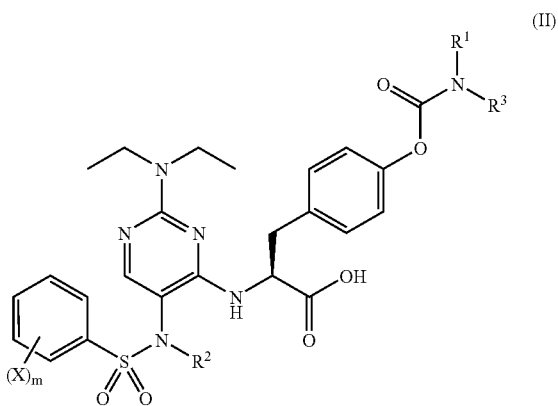

(II)

wherein each X is independently selected from the group consisting of fluoro and chloro;

m is an integer equal to 1 or 2;

$R^2$ is selected from the group consisting of lower alkyl, lower alkenyl, and lower alkylenecycloalkyl;

$R^1$ and $R^3$ together with the nitrogen atom to which they are bound form an azetidinyl, pyrrolidinyl, or piperidinyl group;

and pharmaceutically acceptable salts thereof.

3. A compound of Formula III:

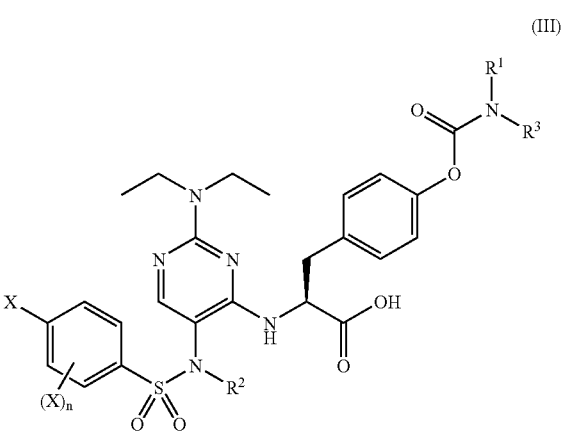

(III)

wherein each X is independently fluoro or chloro;

n is zero or one;

$R^2$ is —$CH_2$—R' where R' is selected from the group consisting of hydrogen, methyl or —CH=$CH_2$;

$R^1$ and $R^3$ together with the nitrogen atom to which they are bound form an azetidinyl, pyrrolidinyl, or piperidnyl group;

and pharmaceutically acceptable salts thereof.

4. A compound of claim 1, wherein $R^1$ and $R^3$ together with the nitrogen atom to which they are bound form an azetidinyl, pyrrolidinyl or piperidinyl group.

5. A compound of any one of claims 1, 2 or 3, wherein $R^2$ is $CH_3$.

6. A compound of claim 3, wherein X is F or Cl, and n is 0.

7. A compound of claim 1 selected from the group consisting of:
   N-(2-[N',N'-diethylamino]-5-[N"-(4-chlorophenylsulfonyl)-N"-ethylamino]pyrimidin-4-yl)-4'-(pyrrolidin-1-ylcarbonyloxy)-L-phenylalanine;
   N-(2-[N',N'-diethylamino]-5-[N"-(4-fluorophenylsulfonyl)-N"-ethylamino]pyrimidin-4-yl)-4'-(pyrrolidin-1-ylcarbonyloxy)-L-phenylalanine;
   N-(2-[N',N'-diethylamino]-5-[N"-(4-fluorophenylsulfonyl)-N"-methylamino]pyrimidin-4-yl)-4'-(pyrrolidin-1-ylcarbonyloxy)-L-phenylalanine;
   N-(2-[N',N'-diethylamino]-5-[N"-(4-chlorophenylsulfonyl)-N"-methylamino]pyrimidin-4-yl)-4'-(pyrrolidin-1-ylcarbonyloxy)-L-phenylalanine;
   N-(2-[N',N'-diethylamino]-5-[N"-(4-fluorophenylsulfonyl)-N"-methylamino]pyrimidin-4-yl)-4'-(piperidin-1-ylcarbonyloxy)-L-phenylalanine;
   N-(2-[N',N'-diethylamino]-5-[N"-(4-fluorophenylsulfonyl)-N"-ethylamino]pyrimidin-4-yl)-4'-(piperidin-1-ylcarbonyloxy)-L-phenylalanine;
   N-(2-[N',N'-diethylamino]-5-[N"-(4-fluorophenylsulfonyl)-N"-ethylamino]pyrimidin-4-yl)-4'-(azetidin-1-ylcarbonyloxy)-L-phenylalanine;
   N-(2-[N',N'-diethylamino]-5-[N"-(4-fluorophenylsulfonyl)-N"-methylamino]pyrimidin-4-yl)-4'-(azetidin-1-ylcarbonyloxy)-L-phenylalanine;
   N-(2-[N',N'-diethylamino]-5-[N"-(4-chlorophenylsulfonyl)-N"-methylamino]pyrimidin-4-yl)-4'-(azetidin-1-ylcarbonyloxy)-L-phenylalanine;
   N-(2-[N',N'-diethylamino]-5-[N"-(4-chlorophenylsulfonyl)-N"-ethylamino]pyrimidin-4-yl)-4'-(azetidin-1-ylcarbonyloxy)-L-phenylalanine;
   N-(2-[N',N'-diethylamino]-5-[N"-(2,4-difluorophenylsulfonyl)-N"-methylamino]-pyrimidin-4-yl)-4'-(pyrrolidin-1-ylcarbonyloxy)-L-phenylalanine;
   N-(2-[N',N'-diethylamino]-5-[N"-(2,4-difluorophenylsulfonyl)-N"-ethylamino]pyrimidin-4-yl)-4'-(pyrrolidin-1-ylcarbonyloxy)-L-phenylalanine;
   N-(2-[N',N'-diethylamino]-5-[N"-(2,4-difluorophenylsulfonyl)-N"-methylamino]-pyrimidin-4-yl)-4'-(azetidin-1-ylcarbonyloxy)-L-phenylalanine;
   N-(2-[N',N'-diethylamino]-5-[N"-(2,4-difluorophenylsulfonyl)-N"-ethylamino]pyrimidin-4-yl)-4'-(azetidin-1-ylcarbonyloxy)-L-phenylalanine; and
   pharmaceutically acceptable salts thereof.

8. A compound of formula (IV):

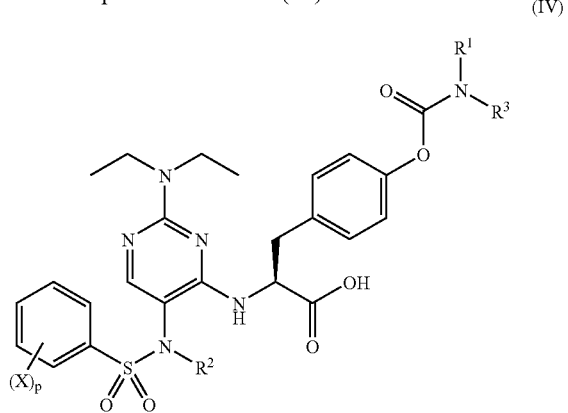

(IV)

wherein each X is independently fluoro, chloro or bromo;
p is an integer from 0 to 3;
$R^1$ and $R^3$ together with the nitrogen atom to which they are bound form an azetidinyl, pyrrolidinyl, pyrrolyl, 2,5-dihydropyrrol-1-yl, piperidinyl, or 1,2,3,6-tetrahydropyridin-1-yl group;
$R^2$ is lower alkynyl;
and pharmaceutically acceptable salts thereof.

9. A compound of Formula V:

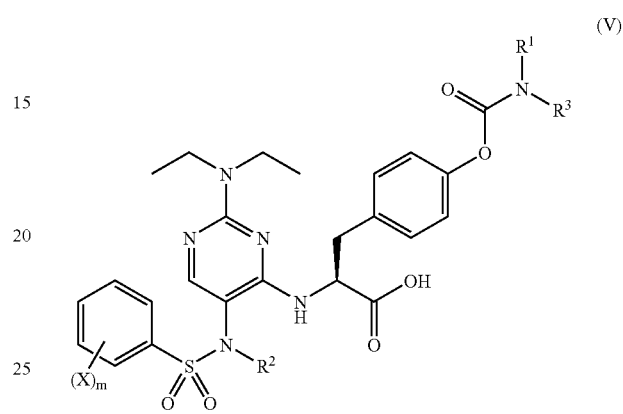

(V)

wherein each X is independently selected from the group consisting of fluoro and chloro;
m is an integer equal to 1 or 2;
$R^2$ is lower alkynyl;
$R^1$ and $R^3$ together with the nitrogen atom to which they are bound form an azetidinyl, pyrrolidinyl, or piperidinyl group;
and pharmaceutically acceptable salts thereof.

10. A compound of Formula VI:

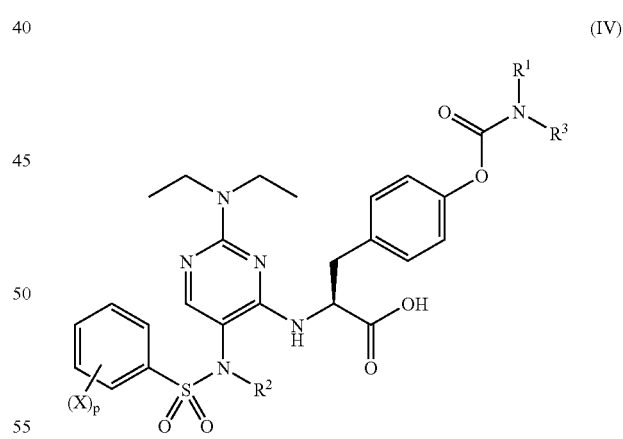

(IV)

wherein each X is independently fluoro or chloro;
n is zero or one;
$R^2$ is lower alkynyl;
$R^1$ and $R^3$ together with the nitrogen atom to which they are bound form an azetidinyl, pyrrolidinyl, or piperidinyl group;
and pharmaceutically acceptable salts thereof.

11. A compound of claim 8, wherein $R^1$ and $R^3$ together with the nitrogen atom to which they are bound form an azetidinyl, pyrrolidinyl, or piperidinyl group.

12. A compound of any one of claims 8, 9, or 10, wherein R² is propargyl.

13. A compound of claim 11, wherein X is F or Cl, and n is 0.

14. A compound of claim 8 selected from the group consisting of

N-(2-[N',N'-diethylamino]-5-[N"-(4-fluorophenylsulfonyl)-N"-propargylamino]pyrimidin-4-yl)-4'-(pyrrolidin-1-ylcarbonyloxy)-L-phenylalanine;

N-(2-[N',N'-diethylamino]-5-[N"-(2,4-difluorophenylsulfonyl)-N"-propargylamino]pyrimidin-4-yl)-4'-(pyrrolidin-1-ylcarbonyloxy)-L-phenylalanine;

N-(2-[N',N'-diethylamino]-5-[N"-(2,4-difluorophenylsulfonyl)-N"-propargylamino]pyrimidin-4-yl)-4'-(azetidin-1-ylcarbonyloxy)-L-phenylalanine;

N-(2-[N',N'-diethylamino]-5-[N"-(4-fluorophenylsulfonyl)-N"-propargylamino]pyrimidin-4-yl)-4'-(azetidin-1-ylcarbonyloxy)-L-phenylalanine;

N-(2-[N',N'-diethylamino]-5-[N"-(4-chlorophenylsulfonyl)-N"-propargylamino]pyrimidin-4-yl)-4'-(pyrrolidin-1-ylcarbonyloxy)-L-phenylalanine; and pharmaceutically acceptable salts thereof.

15. A pharmaceutical composition comprising a pharmaceutically acceptable carrier and a therapeutically effective amount of a compound from any one of claims 1–4, 6, or 7.

16. A pharmaceutical composition comprising a pharmaceutically acceptable carrier and a therapeutically effective amount of a compound according to claim 4.

17. A pharmaceutical composition comprising a pharmaceutically acceptable carrier and a therapeutically effective amount of a compound from anyone of claims 8–11, 13, or 14.

18. A pharmaceutical composition comprising a pharmaceutically acceptable carrier and a therapeutically effective amount of a compound according to claim 12.

* * * * *

UNITED STATES PATENT AND TRADEMARK OFFICE
CERTIFICATE OF CORRECTION

PATENT NO. : 7,026,328 B2  Page 1 of 1
APPLICATION NO. : 10/447308
DATED : April 11, 2006
INVENTOR(S) : Andrei W. Konradi et al.

It is certified that error appears in the above-identified patent and that said Letters Patent is hereby corrected as shown below:

IN THE CLAIMS:

Claim 10 at column 36 line 40-56, replace

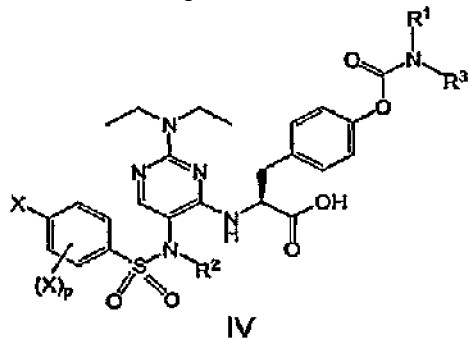

with

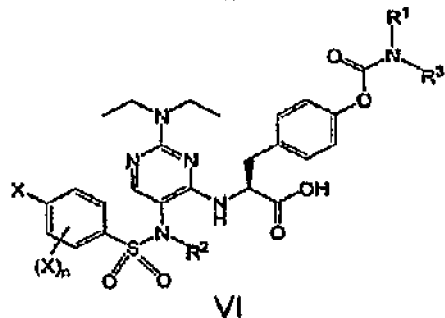

Signed and Sealed this

Second Day of October, 2007

JON W. DUDAS
*Director of the United States Patent and Trademark Office*